United States Patent [19]
Mallet et al.

[11] Patent Number: 5,891,681
[45] Date of Patent: Apr. 6, 1999

[54] MODIFIED PROMOTER FOR RNA POLYMERASE, ITS PREPARATION AND ITS APPLICATIONS

[75] Inventors: Francois Mallet; Francoise Guillou-Bonnici, both of Villeurbanne; Philippe Cleuziat; Pierre Levasseur, both of Lyons, all of France

[73] Assignee: Bio Merieux, Marcy L'Etoille, France

[21] Appl. No.: 360,051

[22] Filed: Dec. 20, 1994

[30] Foreign Application Priority Data

Dec. 22, 1993 [FR] France ................................. 93 15504

[51] Int. Cl.⁶ .............................. C12P 19/34; C12Q 1/68; C07H 21/04
[52] U.S. Cl. ........................... 435/91.1; 435/6; 435/91.1; 435/91.2; 435/91.21; 435/91.5; 536/24.1; 536/24.33; 935/77; 935/78
[58] Field of Search .............................. 435/6, 91.1, 91.2, 435/91.21, 91.5; 536/24.1, 24.33; 935/77, 78

[56] References Cited

U.S. PATENT DOCUMENTS

| 4,952,496 | 8/1990 | Studier et al. | 435/91 |
| 5,037,745 | 8/1991 | McAllister | 435/91 |

FOREIGN PATENT DOCUMENTS

| 0 178 863 | 4/1986 | European Pat. Off. . |
| 0 439 330 A2 | 7/1991 | European Pat. Off. . |
| 88/10315 | 12/1988 | WIPO . |
| 91/02818 | 3/1991 | WIPO . |
| 91/05866 | 5/1991 | WIPO . |

OTHER PUBLICATIONS

C.T. Martin et al., "Kinetic Analysis of T7 RNA Polymerase–Promoter Interactions with Small Synthetic Promoters," Biochemistry, vol. 26, No. 10, 1987, pp. 2690–2696.

J.F. Milligan et al., "Oligoribonucleotide synthesis using T7 RNA polymerase and synthetic DNA templates," Nucleic Acids Research, vol. 15, No. 21, 1987, pp. 8783–8798.

J.E. Brown et al., "Sequences of three promoters for the bacteriophage SP6 RNA polymerase," Nucleic Acids Research, vol. 14, No. 8, 1986, pp. 3521–3526.

(List continued on next page.)

*Primary Examiner*—W. Gary Jones
*Assistant Examiner*—Paul B. Tran
*Attorney, Agent, or Firm*—Oliff & Berridge

[57] ABSTRACT

An oligonucleotide is intended to be used as a promoter non-template strand in the transcription of a sequence of a nucleotide target in the presence of a phage RNA polymerase. The phage RNA polymerase has specific natural promoters containing a consensus sequence from at least position −17 to position −1. The oligonucleotide contains a core sequence flanked at at least one of its ends by a nucleotide sequence capable of hybridization with a sequence of the target. The core sequence contains a sequence of 6 to 9 consecutive nucleotides from the region −12 to −4 of the non-template strand of the specific promoter, or a sufficiently homologous sequence to enable the functionality of the RNA polymerase to be retained. One flanking sequence is complementary to a first region of the target, and a second flanking sequence, when present, is complementary to a second region of the target, the first and second regions being separated on the target by a sequence having a number of nucleotides equal to the number of nucleotides in the core sequence. The number of nucleotides in the flanking region, or the sum of the number of nucleotides in the flanking regions, is at least sufficiently high for the nucleotide to be able to hybridize with the target at the temperature of use of the RNA polymerase. Such an oligonucleotide enables transcription to be initiated at a site of the target which is not normally a transcription start site for the RNA polymerase.

16 Claims, 12 Drawing Sheets

```
(SEQ ID NO:60)  5'  TAGAAGTAAACATA TAATACGACTCACTATAG GCATTAGGAAT 3'
                    ||||||||||||||  |  ||||||| |||  |||||||||||
(SEQ ID NO:61)  3' ...ATCTTCATTTGTAT CATTGTCTGAGTGTTATA CGTAATCCTTA... 5'
                              phage RNA polymerase
                              + rNTPs
                                        (SEQ ID NO:62)  UGCAUUAGGAAU... 3'
                                                         RNA (SEQ ID NO:63)  5'  CTCAGGTCACTCTTT TAATACGACTCACTATAG CAATAAAGAT 3'
                    |||||||||||||||  |||||| |   |  |||||||||
(SEQ ID NO:64)  3' ...GAGTCCAGTGAGAAA CCGTTGCTGGGGAGCAGT GTTATTTCTA...5'
                              phage RNA polymerase
                              + rNTPs
                                        (SEQ ID NO:65)  ACAAUAAAGAU...3'
                                                         RNA
```

OTHER PUBLICATIONS

K.A. Chapman et al., "Construction of bacteriophage T7 late promoters with point mutations and characterization by in vitro transcription properties," Nucleic Acids Research, vol. 15, No. 13, 1987, pp. 5413–5432.

G.A. Diaz et al., "Hierarchy of Base–pair Preference in the Binding Domain of the Bacteriophage T7 Promoter," Journal of Molecular Biology, vol. 229, 1993, pp. 805–811.

R.A. Ikeda, "The Efficiency of Promoter Clearance Distinguishes T7 Class II and Class III Promoters," The Journal of Biological Chemistry, vol. 267, No. 16, 1992, pp. 11322–11328.

R.A. Ikeda et al., "Initiation of Transcription by T7 RNA Polymerase at its Natural Promoters," The Journal of Biological Chemistry, vol. 267, No. 4, 1992, pp. 2640–2649.

K.A. Chapman et al., "Bacteriophage T7 late promoters with point mutations: quantitative footprinting and in vivo expression," Nucleic Acids Research, vol. 16, No. 10, 1988, pp. 4511–4524.

J.J. Dunn et al., "Complete Nucleotide Sequence of Bacteriophage T7 DNA and the Locations of T7 Genetic Elements," Journal of Molecular Biology vol. 166, 1983 pp. 477–535.

H.L. Osterman et al., "T7 Ribonucleic Acid Polymerase–Promoter Interactions," Biochemistry, vol. 20, No. 17, 1981, pp. 4884–4892.

J.E. Brown et al., "Sequences of three promoters for the bacteriophage SP6 RNA polymerase," Nucleic Acids Research, vol. 14 No. 8, 1986, pp. 5321–5326.

E.T. Schenborn et al., "A novel transcription property of SP6 and T7 RNA polymerases: dependence on template structure," Nucleic Acids Research, vol. 13, No. 17, 1985, pp. 6223–6236.

J.N. Bailey et al., "Relationship between promoter structure and template specificities exhibited by the bacteriophage T3 and T7 RNA polymerases," Proc. Natl. Acad. Sci. USA, vol. 80, pp. 2814–2818, May 1983 Biochemistry.

Krupp et al. FEBS Letters (1987) 212(2): 271–275.

Promega Product Catalogue (1994/1994) p. 87.

COMPARISON OF THE CONSENSUS SEQUENCES OF THE PROMOTERS FOR T7, T3 AND SP6 RNA POLYMERASES

```
                     -10        +1
T3        TATTAACCCTCACTAAAGGGAGA    (SEQ ID NO:28)
          ||  |||||     |  |||  |
SP6       ATTTAGGTGACACTATAGAAGGG    (SEQ ID NO:40)
          |||  |  |||        ||| |
T7        TAATACGACTCACTATAGGGAGA    (SEQ ID NO:10)
           |   |||        |
T3        TATTAACCCTCACTAAAGGGAGA    (SEQ ID NO:28)
           |    ||| |     |
K11       AATTAGGGCACACTATAGGGAGA    (SEQ ID NO:55)
          | |  | | |      |||  |
BA14      TAATACGACTCACTAATGCGAGA    (SEQ ID NO:56)

consensus TATTAGG-CTCACTATAGGGAGG    (SEQ ID NO:57)
```

| SOMETIMES DIFFERENT

| ALWAYS DIFFERENT

| SEQ ID:NO | NAME | DNA STRUCTURES | LENGTH OF DNA STRAND+ STRAND− | LENGTH OF RNAs TRANSCRIBED | | | | |
|---|---|---|---|---|---|---|---|---|
| | | | | 26b | 29b | 50b | 53b | 58b |
| 1 | E+ | TAATA ATA·G | 41 | | b ••• | | | |
| 2 | E− | ATTAT TAT·C | 58 | | ••• | | | |
| 6 | US+ | ATA·G | 36 | | b ••• | | | |
| 3 | US− | TAT·C | 53 | | ••• | | | |
| 6 | US+ | ATA·G | 36 | a ••• | | | | |
| 5 | UD− | TAT·C | 50 | a •• | | | | |
| 8 | UD+ | G | 33 | | | | | |
| 5 | UD− | C | 50 | | | | | |
| 1 | E+ | TAATA ATA·G | 41 | | | | | |
| 6 | US+ | ATA·G | 36 | | | | | |
| 8 | UD+ | G | 33 | | | | | |
| 2 | E− | ATTAT TAT·C | 58 | b ••• | | | | c ••• |
| 3 | US− | TAT·C | 53 | b •• | | | d ••• | |
| 5 | UD− | C | 50 | | | | | c ••• |

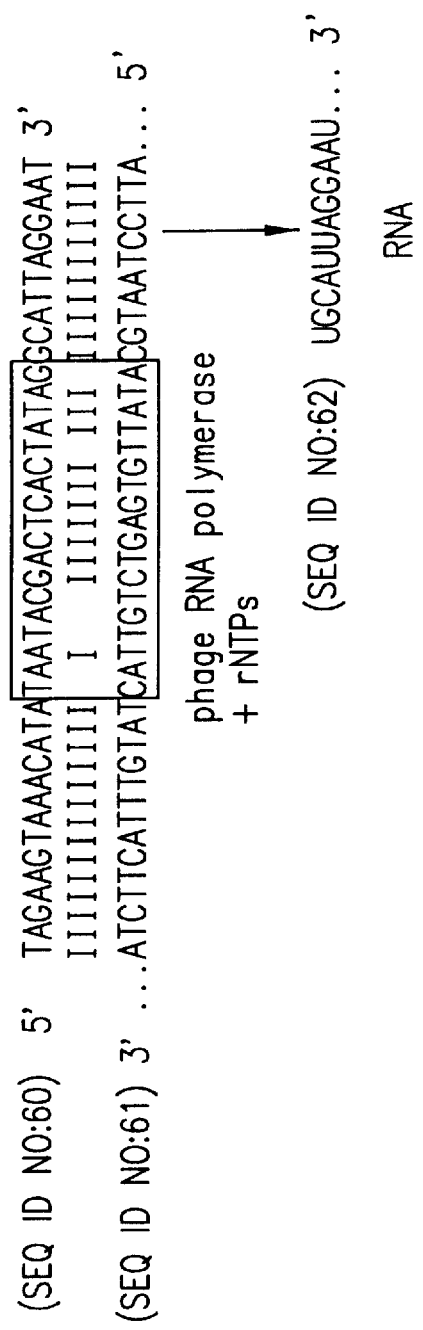

MODIFIED PROMOTER FOR RNA POLYMERASE, ITS PREPARATION AND ITS APPLICATIONS

BACKGROUND

The present invention relates to a modified promoter for RNA polymerase and to its applications. More especially, it relates to the use of a promoter for phage RNA polymerases, this promoter being modified relative to the promoters present in nature or which have already been described. It has been discovered that it is possible to reduce the size of the promoter sequence and to integrate mispairings between the two strands of the promoter. The modified promoters obtained according to the invention make it possible, in particular, to effect the transcription of a nucleotide target from a site which is not normally a transcription start site for the RNA polymerase used. By means of the invention, it becomes possible to transcribe in vitro a wide diversity of sequences which are not transcribed by phage RNA polymerases when the wild-type promoters (that is to say the natural promoters) of the said RNA polymerases are used. The use of these modified promoters makes it possible, furthermore, to obtain different efficiencies of initiation of transcription for the differential transcription of several sequences within a same reaction medium.

RNA (ribonucleic acid) is known to be the transcription product of a molecule of DNA (deoxyribonucleic acid) synthesized under the action of an enzyme, DNA-dependent RNA polymerase.

It is advantageous in several respects to be able to obtain several RNA sequences from a DNA sequence. Different applications of the obtaining of specific RNA sequences have already been described, such as, for example, the synthesis of RNA probes or of oligoribonucleotides (see, in particular, Milligan, J. F., Groebe, D. R., Witherell, G. W. and Uhlenbeck, O. C. (1987) Nucleic Acids Res. 25, 8783–8798), or the expression of genes (see, in particular, Steen, R. et al. (1986) EMBO J. 5, 1099–1103 and Fuerst, T. R. et al. (1987) Molecular and Cellular Probes 7, 2538–2544 and Patent Applications WO 91/05,866 and EP 0,178,863), or alternatively gene amplification as described by Kievits, T. et al. (Journal of Virological Methods 35, 273–286 (1991)) and Kwoh, D. Y. et al. (Proc. Natl. Acad. Sci. USA 86, 1173–1177 (1989)) or in Patent Applications WO 88/10,315 and WO 91/02,818.

One of the distinctive features of DNA-dependent RNA polymerases is that of initiating RNA synthesis according to a DNA template from a particular start site as a result of the recognition of a nucleic acid sequence, termed promoter, which makes it possible to define the precise localization and the strand on which initiation is to be effected. Contrary to DNA-dependent DNA polymerases, polymerization by DNA-dependent RNA polymerases is not initiated from a 3'-OH end, and their natural substrate is an intact DNA double strand.

A few generic terms which will be employed are defined below.

Oligonucleotide or polynucleotide is understood to mean nucleotide sequences containing the natural bases (A, C, G, T, U) and/or one or more modified bases such as inosine, 5-methyldeoxycytidine, deoxyuridine, 5-(dimethylamino) deoxyuridine, 2,6-diaminopurine, 5-bromodeoxyuridine or all modified bases permitting hybridization, especially those modified by all suitable chemical modifications enabling the hybridization yield to be increased. Examples of such modifications are, in particular, the introduction between at least two nucleotides of a group chosen from diphosphate, alkyl- and/or arylphosphonate and/or phosphorothioate esters, or the replacement of at least one sugar (ribose or deoxyribose) by a polyamide; see, for example, Nielsen, P. E. et al., Science, 254, 1497–1500 (1991). The term "nucleotide" or "base" denotes not only a natural deoxyribonucleotide or ribonucleotide, but any nucleotide modified as has just been mentioned.

Promoter is understood to mean any nucleic acid sequence capable of being recognized by an RNA polymerase to initiate transcription, that is to say the synthesis of an RNA. This RNA polymerase can be either DNA-dependent or RNA-dependent.

Natural promoter is understood to mean the promoter sequences present in the genome, coding for the RNA polymerase for which this promoter is specific. Promoter sequence is understood to mean the sequence of an oligonucleotide which participates in the composition of one of the strands of the promoter.

Transcription is understood to mean the neosynthesis of several RNA strands complementary to the sequence (or target) which is under the control of the promoter, the promoter permitting initiation of this reaction. This sequence is in general adjacent to the 5' end of the template strand of the promoter. The RNA strands synthesized are termed transcripts.

Differential transcription is understood to mean a transcription giving different numbers of transcripts from different templates.

Mutation is understood to mean any change in sequence relative to the natural sequence. The mutation can affect both complementary bases positioned on each strand of a nucleic acid duplex, or affect only one of them. If the mutation affects only one of the two complementary bases, it gives rise to the appearance of what is called a mispairing.

Mispairing is understood to mean the introduction within a nucleic acid double strand of pairs of bases other than A:T, C:G or A:U.

Non-pairing is understood to mean the presence of nucleotides which are not paired with a base of the complementary nucleic acid strand, by virtue of their nature or by virtue of their position in the sequence. If several bases of the same strand are unpaired, they can form bonds with one another which can cause the appearance of secondary structures termed "loops" or "stem-loops".

Deletion is understood to mean the removal of some nucleotides from a sequence. A deletion can affect only one base, or several adjacent bases. If several non-adjacent bases are affected, this will be referred to as multiple deletions. On a double-stranded nucleic acid, a deletion generally affects, together, both complementary bases positioned on each nucleic acid strand. However, a deletion can also take place only on one or several bases of only one strand, and cause non-pairings.

Consensus sequence is understood to mean a theoretical nucleotide sequence in which the nucleotide at each site is the one which appears most commonly at this site in the different natural forms of the genetic element in question (for example the promoter). The term "consensus" also denotes any actual sequence very closely similar to the theoretical consensus sequence.

It will be recalled that transcription takes place by synthesis, in the 5'→3' direction, of an antiparallel RNA complementary to the nucleotide strand transcribed (termed "template strand" or "antisense strand"). The DNA strand which is complementary to the transcribed strand is termed "non-template strand" or "sense strand". By convention, the nucleotide from which transcription starts is designated +1 (or simply 1). On the template strand, the successive nucleotides located beside the 3' end (upstream region) are, starting from +1, numbered −1, −2, and the like. A downstream region relative to a given nucleotide (or to a given sequence) is located towards the 5' end of the template strand, and hence towards the 3' end of the RNA strand synthesized. Starting from +1, nucleotides downstream correspond successively to positions +2, +3, and the like.

Compared to bacterial, eukaryotic or mitochondrial RNA polymerases, phage RNA polymerases are very simple enzymes. Among these, the best known are the RNA polymerases of bacteriophages T7, T3 and SP6. Bacteriophage T7 RNA polymerase has been cloned (see, in particular, U.S. Pat. No. 4,952,496). These enzymes are very homologous with one another, and are composed of a single subunit of 98 to 100 kDa. Two other phage polymerases share these homologies: that of Klebsiella phage K11 and that of phage BA14; see Diaz et al., *J. Mol. Biol.* 229: 805–811 (1993).

The natural promoters specific for the RNA polymerases of phages T7, T3 and SP6 are well known. Sequencing of the whole bacteriophage T7 genome in 1983 by Dunn et al. (*J. Mol. Biol.* 166, 477–535 (1983)) enabled the existence of 17 promoters to be defined on this DNA, these being shown in Table 1 below (non-template strand).

As is apparent from the above table, twenty-three adjacent nucleotides located between positions −17 and +6 relative to the transcription start site (position 1) are highly conserved. These nucleotides are even identical in the 5 class III promoters, which are the most efficient in vivo and in vitro. Among the 11 different promoters, the majority diverge in respect of the nucleotides lying between positions +3 and +6. Among the nucleotides lying between positions −16 and −1, nine are completely conserved, and four others are conserved in 16 promoters. These findings suggest that these 13 nucleotides are important factors in the definition of a promoter. These conclusions have been confirmed by demonstrating the efficacy of a promoter after cleavage of the DNA upstream of position −21 (Osterman, H. L. et al. (1981) *Biochemistry* 20, 4884–4892) and −17 (Martin, C. T. et al. (1987) *Biochemistry* 26, 2690–2696). In contrast, these same publications show that a cleavage upstream of −10 or −12 abolishes this efficacy.

Phage T3 RNA polymerase is almost as well known as T7 RNA polymerase. These two enzymes have a very similar structure (80% identity) (McGraw, N. J. et al. (1985) *Nucleic Acids Res.* 13, 6753–6766), but possess, however, an almost absolute template specificity. The sequences of 11 promoters specific for T3 RNA polymerase have been determined and are presented in Table 2 below (non-template strand).

TABLE 1

Promoters for T7 RNA polymerase

| Promoter | Nucleotide | | | |
|---|---|---|---|---|
| | | −10 | 1 | |
| Conserved sequence | | TAATACGACTCACTATAGGGAGA | | (SEQ ID NO:10) |
| Replication promoter | −20 | −10 | 1 | |
| φOL | TTGTCTTTAT | TAATACAACTCACTATAAGGAGA | GA | (SEQ ID NO:11) |
| Class II promoters | −20 | −10 | 1 | |
| φ1-1A | AACGCCAAAT | CAATACGACTCACTATAGAGGGA | CA | (SEQ ID NO:12) |
| φ1-1B | TTCTTCCGGT | TAATACGACTCACTATAGGAGGA | CC | (SEQ ID NO:13) |
| φ1-3 | GGACTGGAAG | TAATACGACTCAGTATAGGGACA | AT | (SEQ ID NO:14) |
| φ1-5 | AGTTAACTGG | TAATACGACTCACTAAAGGAGGT | AC | (SEQ ID NO:15) |
| φ1-6 | TGGTCACGCT | TAATACGACTCACTAAAGGAGAC | AC | (SEQ ID NO:16) |
| φ2-5 | AGCACCGAAG | TAATACGACTCACTATTAGGGAA | GA | (SEQ ID NO:17) |
| φ3-8 | CGTGGATAAT | TAATTGAACTCACTATTAGGGAA | GA | (SEQ ID NO:18) |
| φ4c | CCGACTGAGA | CAATCCGACTCACTAAAGAGAGA | GA | (SEQ ID NO:19) |
| φ4-3 | AGTCCCATTC | TAATACGACTCACTAAAGGAGAG | AC | (SEQ ID NO:20) |
| φ4-7 | TTCATGAATA | CTATTCGACTCACTATAGGAGAT | AT | (SEQ ID NO:21) |
| Class III promoters | −20 | −10 | 1 | |
| φ6-5 | GTCCCTAAAT | TAATACGACTCACTATAGGGAGA | TA | (SEQ ID NO:22) |
| φ9 | GCCGGGAATT | TAATACGACTCACTATAGGGAGA | CC | (SEQ ID NO:23) |
| φ10 | ACTTCGAAAT | TAATACGACTCACTATAGGGAGA | CC | (SEQ ID NO:24) |
| φ13 | GGCTCGAAAT | TAATACGACTCACTATAGGGAGA | AC | (SEQ ID NO:25) |
| φ17 | GCGTACCAAA | TAATACGACTCACTATAGGGAGA | GG | (SEQ ID NO:26) |
| Replication promoter | −20 | −10 | 1 | |
| φOR | CACGATAAAT | TAATACGACTCACTATAGGGAGA | GG | (SEQ ID NO:27) |

TABLE 2

Promoters for T3 RNA polymerase

| Promoter | | Nucleotide | | |
|---|---|---|---|---|
| | −20 | −10 | 1 | |
| Conserved sequence | | TATTAACCCTCACTAAAGGGAGA | | (SEQ ID NO:28) |
| | −20 | −10 | 1 | |
| | GTC | TATTTACCCTCACTAAAGGGAAT | AAGG | (SEQ ID NO:29) |
| | TAG | CATTAACCCTCACTAACGGGAGA | CTAC | (SEQ ID NO:30) |
| | TAC | AGTTAACCCTGACTAACGGGAGA | GTTA | (SEQ ID NO:31) |
| | AAG | TAATAACCCTCACTAACAGGAGA | ATCC | (SEQ ID NO:32) |
| | GGG | CATTAACCCTCACTAACAGGAGA | CACA | (SEQ ID NO:33) |
| | GCC | TAATTACCCTCACTAAAGGGAAC | AACC | (SEQ ID NO:34) |
| | TAC | AATTAACCCTCACTAAAGGGAAG | AGGG | (SEQ ID NO:35) |
| | TCT | AATTAACCCTCACTAAAGGGAGA | GACC | (SEQ ID NO:36) |
| | ACC | TAATTACCCTCACTAAAGGGAGA | CCTC | (SEQ ID NO:37) |
| | GTG | AATTAACCCTCACTAAAGGGAGA | CACT | (SEQ ID NO:38) |
| | TTG | CATTAACCCTCACTAAAGGGAGA | GAGG | (SEQ ID NO:39) |

At the present time, 4 different sequences of promoters for phage SP6 RNA polymerase have been demonstrated by Brown, J. E., et al. (*Nucleic Acids Res.* 14, 3521–3526) (1986)). Phage SP6 RNA polymerase also displays many similarities with phage T7 RNA polymerase. These sequences are presented in Table 3 below (non-template strand).

TABLE 3

Promoters for SP6 RNA polymerase

| Promoter | | Nucleotide | | |
|---|---|---|---|---|
| | | −10 | 1 | |
| Conserved sequence | | ATTTAGGTGACACTATAGAAGGG | | (SEQ ID NO:40) |
| | −20 | −10 | 1 | |
| pSF64 | ACACATACG | ATTTAGGTGACACTATAGAATAC | AA | (SEQ ID NO:41) |
| pJEB1 | TAATTGCCT | ATTTAGGTGACACTATAGAAGGG | AG | (SEQ ID NO:42) |
| pJEB4 | GGACTTGGT | AATTAGGGGACACTATAGAAGGA | GG | (SEQ ID NO:43) |
| pJEB6 | GTGTCTCTT | ATTTAGGGGACACTATAGAAGAG | AG | (SEQ ID NO:44) |

As is the case for T7 RNA polymerase, the sequences of the promoters for T3 RNA polymerase and for SP6 RNA polymerase are very similar, in particular between positions −17 and +6. Comparison of the sequences of these three promoters (FIG. 1) shows the existence of a common sequence from position −7 to −3; see in this connection, in particular: Brown, J. E. et al., *Nucleic Acid Res.*, 14, 3521–3526 (1986) and Bailey et al., *Proc. Natl. Acad. Sci. USA* 80: 2814–2818 (1983).

Hence it is possible to consider that the various phage RNA polymerases studied above belong to a family of RNA polymerases which recognize promoters possessing a consensus sequence from position −17 to position +6, and in particular from −17 to −1.

To obtain the RNA corresponding to a given DNA sequence through the action of an RNA polymerase, it is necessary to place this sequence under the control of the promoter of this RNA polymerase. This is the so-called step of installation of a promoter, immediately upstream of the sequence to be transcribed. This installation in the present state of the art requires the use of laborious methods.

The most traditional method of installation of a promoter is the cloning of the sequence to be transcribed into a vector containing a promoter for a phage RNA polymerase upstream of a cloning site. Several vectors of this type are on the market, such as, for example, pT3/T7-LUC (Clontech Laboratories Inc.), or Lambda ZAP II, Uni-ZAP XR, Lambda DASH II, Lambda FIX II, pWE 15 and SuperCos cosmid (Stratagene Cloning System), or pT7-0, pT71 or pT7-2 (United States Biochemical) or alternatively pT7/T3a-18 or pT7/T3a-19 (GIBCO BRL), or are described in publications, such as the pET vectors (Rosenberg, A. H. et al., *Gene* 56, 125–135 (1987)). After the DNA fragment to be cloned has been obtained and inserted into the vector, and the vector has been amplified, transcription may be effected. This method enables any sequence to be transcribed. However, it is very laborious, and not every kind of end can be obtained on the RNA in this way, since the localization of this end is imposed by the enzyme restriction site used for the cloning.

Some known methods for the in vitro synthesis of oligoribonucleotides require the synthesis by chemical means of two complementary oligodeoxynucleotides comprising a promoter for a phage RNA polymerase. It has been demonstrated (Milligan et al., paper cited) that a partially single-stranded template which is double-stranded only on the promoter sequence, from position +1 to −14, is as active in transcription as a double-stranded template. Thus, the method requires the synthesis of a 15-mer nucleotide comprising the sequence of the non-template strand of a phage promoter from position −14 to +1, and of a second oligonucleotide containing at its 3' end the sequence complementary to the first oligonucleotide, and on its 5' region the sequence complementary to the oligoribonucleotide which it is desired to synthesize. Since chemical synthesis does not enable oligonucleotides of good quality to be obtained if their size is larger than 70 bases, this technique is not applicable for oligoribonucleotides of more than 55 bases if the promoter sequences already described are used. Furthermore, the method requires exact knowledge of the RNA sequence which it is desired to synthesize.

Another method of installation of a promoter on a sequence, by ligation, is possible (Leary, S. et al., Gene 106, 93–96 (1991)) if this sequence possesses a well-defined 3' end. It comprises the hybridization with this 3' end of an oligonucleotide carrying the sequence of the non-template strand of the promoter, followed by the sequence complementary to the 3' end of the target sequence, over a sufficient length to permit hybridization. A second oligonucleotide is involved, the sequence of which is complementary to the promoter region of the first oligonucleotide, and which carries a phosphate group at the 5' end. Hybridization of these two oligonucleotides and the target brings the 5'-phosphate end of the oligonucleotide carrying the sequence of the template strand of the promoter into contact with the 3'-OH end of the target. Through the action of a ligase, a phosphodiester link between these two ends is established, permitting the formation of a complex in which the target is under the control of the promoter.

The appearance of the "polymerase chain reaction" (PCR) technique has made possible the creation of new, more efficacious methods for installing a promoter. The transcription template is synthesized by PCR. The upstream primer supplies the promoter for the phage RNA polymerase and defines the 5' end of the transcription product (or transcript), while the downstream primer defines the 3' end of the amplified DNA and of the transcript. This technique enables an RNA of any size and with any 3' end to be obtained.

The installation of a phage promoter by means of a reaction modelled on the cycle of retroviruses is possible from an RNA (Kwoh, D. Y. et al., P.N.A.S. USA, 86, 1173–1177 (1989)). An upstream primer carrying the sequence of the promoter is used to synthesize the DNA complementary to the RNA by means of a reverse transcriptase. The RNA of the RNA:DNA duplex thereby formed is digested with RNaseH. The single-stranded DNA thus liberated hybridizes with the second primer which, by means of the reverse transcriptase, enables the second complementary DNA strand to be synthesized. However, this first step does not enable the 3' end of the RNA to be defined. It is the second synthesis, with the same enzymes and by the same method, of a second generation of template for the phage RNA, from the first transcripts obtained, which enables a 3' end to be obtained which is strictly defined by the second primer used.

SUMMARY OF THE INVENTION

One of the objects of the invention is to reduce as far as possible the difficulties of installation of the promoter, using modified promoters of short sequence, making it possible to reduce the sequence constraints on the target sequence to be transcribed. The invention also enables promoters of different efficiencies to be obtained, which are usable for the transcription of different sequences at different levels in the same reaction medium.

The use of the modified promoters according to the invention enables the transcription of any nucleic acid sequence, deoxyribonucleic or ribonucleic, to be obtained.

The subject of the invention is hence an oligonucleotide which is usable as a promoter non-template strand, in the transcription of a sequence of a nucleotide target, in the presence of a phage RNA polymerase having a specific natural promoter, from a site of the said target which is not normally a transcription start site for the said phage RNA polymerase, which polymerase is chosen from those of the phages whose RNA polymerases have specific promoters comprising a consensus sequence at least from position −17 to position −1, characterized:

- in that it comprises a core sequence flanked at one of its ends at least by a nucleotide sequence capable of hybridization with a sequence of the target,
- in that the said core sequence consists of a sequence of 6 to 9 consecutive nucleotides chosen from the region −12 to −4 of the non-template strand of the said specific promoter, or a sufficiently homologous sequence enabling the functionality of the said RNA polymerase to be retained,
- in that one flanking sequence is complementary to a first region of the target, and in that the other flanking sequence, when it is present, is complementary to a second region of the target, the said first and second regions being separated on the target by a sequence having a number of nucleotides equal to the number of nucleotides in the core sequence,
- and in that the number of nucleotides in the flanking region, or the sum of the number of nucleotides in the flanking regions, is at least sufficiently high for the said oligonucleotide to be able to hybridize with the target at the temperature of use of the RNA polymerase.

DESCRIPTION OF PREFERRED EMBODIMENTS

Phage RNA polymerases displaying the features mentioned above are of the type containing only one subunit and having a molecular mass in the region of 100 kDa. The invention naturally extends to the use of viral, non-phage, RNA polymerases displaying similar features, and to the modification of the promoters specific for the said viral RNA polymerases.

It has, in effect, been discovered that a short sequence such as the core sequence mentioned above is capable of functioning as a promoter of RNA polymerase. This discovery is of a surprising nature, inasmuch as the larger part of the core sequence, as defined above, corresponds to highly variable sequences of the wild-type promoters, in particular between positions −8 and −12, as shown by examination of FIG. 1.

Since the core sequence is relatively short, this increases the chances of randomly encountering a target sequence, a sequence complementary to the core sequence, or which is sufficiently complementary to the core sequence to permit at least partial hybridization with the latter. This results in a possibility of effecting a transcription at a site which is not normally a transcription start site with the unmodified wild-type promoter. This possibility is further increased by the presence of the flanking region or flanking regions, which are complementary by construction to the target, and which contribute considerably to the hybridization of the modified promoter with the target.

Preferably, the core sequence is chosen from sequences of 6 to 9 nucleotides of an existing natural promoter. However, homologous sequences differing, for example, by one or two nucleotides relative to the natural promoter may also be used, in particular to improve, where appropriate, the pairing of the core sequence with the corresponding sequence of the target, inasmuch as the core sequence is sufficiently homologous with the corresponding natural sequence to retain the functionality of the enzyme, that is to say inasmuch as the enzyme can function with a promoter having a core sequence thus modified, which can be readily checked by simple routine experiments.

The oligonucleotide according to the invention can consist of natural bases, deoxyribonucleic or ribonucleic, or consist at least in part of modified bases. It can consist, in particular, of oligonucleotides modified by coupling with psoralen, or alternatively consist of PNA (peptide nucleic acids).

When two flanking sequences are present upstream and downstream, respectively, of the core sequence, they are complementary to two regions of the target spaced apart on the target by a number of nucleotides equal to the number of nucleotides in the core sequence.

As a result of the flanking region or flanking regions, hybridization of the oligonucleotide with the target generally enables transcription to be effected, even in the case where the core sequence is not even partially complementary to the region opposite to it on the target in the target-oligonucleotide duplex. This possibility is further increased with the use of modified bases for producing the core sequence and/or flanking sequences.

Hence the invention makes it possible to effect the transcription of any sequence of a given target by making the transcription start at a site which would not normally be a transcription start site for an unmodified promoter.

According to a preferred embodiment, the oligonucleotide of the invention contains an upstream flanking region in which the number of nucleotides is such that the sum of the numbers of nucleotides in the core sequence and in the upstream flanking sequence is equal to at least 10, and especially equal to at least 11. Each flanking region preferably contains at least 5 nucleotides, and especially from 5 to 12 nucleotides.

The sequence −12 to −4, from which the core sequence may be chosen, is, in particular, one of the sequences −12 to −4 of the non-template strand of a wild-type promoter. Such sequences −12 to −4 are, for example, the following:

| - GGTGACACT | (SEQ ID NO:45) |
|---|---|
| - CGACTCACT | (SEQ ID NO:46) |
| - ACCCTCACT | (SEQ ID NO:47) |
| - GGGCACACT | (SEQ ID NO:48) |
| - CAACTCACT | (SEQ ID NO:49) |
| - CGACTCAGT | (SEQ ID NO:50) |
| - GAACTCACT | (SEQ ID NO:51) |

As mentioned above, the core sequence may be chosen from within the sequences −12 to −4 of wild-type promoters.

It will be readily appreciated that the yield of the transcription may vary in accordance with the sequences used as core sequences. It is, however, possible, by selection by means of simple routine experiments involving transcription tests, to construct a modified promoter enabling transcription to be effected with a yield at least equal to a predetermined threshold.

Naturally, oligonucleotides having a core sequence corresponding to a sequence of a natural promoter, and having upstream and downstream sequences fortuitously present in the said natural promoter, do not form part of the invention.

The subject of the invention is also a method for preparing an oligonucleotide which is usable as a modified promoter for RNA polymerase, characterized in that an oligonucleotide as has been defined above is synthesized according to methods known per se.

The present invention enables any sequence to be placed under the control of such a modified promoter. The methods used for this purpose are, in particular, methods already known per se, and especially the following:

(1) cloning of the sequence of such a promoter upstream of a cloning site into a plasmid expression vector, thereafter enabling the sequence which it is desired to transcribe to be cloned into this vector under the control of this promoter;

(2) synthesis of an oligonucleotide comprising the sequence of the non-template strand of a modified promoter, and of a second oligonucleotide containing at its 3' end the sequence complementary to the first oligonucleotide, and at its 5' end the sequence complementary to the oligoribonucleotide which it is desired to synthesize. Since chemical synthesis is limited as regards the maximum size of the oligonucleotides, the use of promoters of shorter sequence makes it possible to synthesize oligoribonucleotides which are longer than when the natural promoter sequences are used;

(3) synthesis of a transcription template by a polymerization chain reaction, the upstream primer supplying the modified promoter and defining the 5' end of the transcript, and the downstream primer defining the 3' end of the amplified DNA and of the transcript;

(4) synthesis of a transcription template by elongation, using a reverse transcriptase, of an upstream primer carrying the sequence of the modified promoter hybridized with an RNA, digestion with RNase H of the RNA contained in the RNA:DNA duplex thereby formed, and hybridization of the single-stranded DNA thus liberated with the second primer which, by elongation using reverse transcriptase, permits the synthesis of the second strand of the template and of the modified promoter;

(5) installation, by ligation, of a modified promoter on a deoxyribonucleic acid sequence or a ribonucleic acid if this sequence possesses a well-defined 3' end, by hybridization with this 3' end of an oligonucleotide carrying the non-template strand of the modified promoter, followed by the sequence complementary to the 3' end of the target sequence, over a sufficient length for hybridization, and hybridization with this first oligonucleotide of a second oligonucleotide whose sequence is complementary to the modified promoter region of the first oligonucleotide, and which carries a phosphate group at the 5' end. Hybridization of the two oligonucleotides and the target brings the 5'-phosphate end of the oligonucleotide carrying the sequence of the template strand of the promoter into contact with the 3'-OH end of the target. The action of a ligase then permits the formation of a complex in which the target is under the control of the modified promoter.

The present invention also relates to the installation of any sequence under the control of a modified promoter, by a method, described below, based on the use of double-stranded sequences which are shorter than the wild-type sequence of the promoter, and/or which display mispairings brought about by mutations on the non-coding strand, and/or which display non-pairings due to one or more deletion(s) on the template strand of the promoter, and/or which carry other modifications. In particular, the present invention relates to the simplified installation of a promoter for an RNA polymerase upstream of a nucleic acid (termed target) of given sequence, of a deoxyribonucleic acid or ribonucleic acid nature, so as to permit the transcription of this sequence by the RNA polymerase in question.

The method consists in hybridizing, with the 3' region of the sequence to be transcribed and with the region immediately adjacent on the 3' side of this sequence, an oligonucleotide of sequence partially or wholly complementary to the target, but which is capable of hybridizing with the target at the temperature of use of the RNA polymerase.

The oligonucleotide hybridizes at least partially with the target as a result of the hybridization of at least the flanking sequence (or flanking sequences) with the target.

The "core" region can hence display non-pairings or mispairings with the target, that is to say regions which, by virtue of their sequence or their position, are not in hybridization contact with the template strand of the target. In effect, the hybridization of the oligonucleotide, as a result of the flanking sequence or flanking sequences, with the regions of the target which are complementary to them, permits juxtaposition of the "core" sequence with a sequence, possibly of any kind, of the target.

The invention also relates to the use of the above modified promoter, as a promoter non-template strand in the transcription of a sequence of a nucleotide target capable of hybridizing with the said oligonucleotide.

For implementation of this use, the oligonucleotide should be brought into contact with the target under conditions permitting transcription, which can take place in several ways, and in particular as follows:

(1) If the target nucleic acid is a single strand, hybridization may be effected by mixing the target with the oligonucleotide, in solution in a buffer which is preferably the buffer in which the transcription reaction will take place, at a temperature permitting hybridization;

(2) If the target nucleic acid is a double strand, hybridization may be effected as follows:

(2.1) If the oligonucleotide is an unmodified oligonucleotide, the target will have to be denatured before being hybridized with the oligonucleotide under the conditions described in paragraph (1). The denaturation may be effected according to known methods, especially by heat (incubation for 5 minutes at 95° C.), or alternatively by alkaline treatment (0.1M NaOH for 5 minutes) followed by neutralization before hybridization with the oligonucleotide;

(2.2) If the oligonucleotide is a modified oligonucleotide, and especially a PNA, hybridization does not necessitate prior denaturation of the target. Sequences consisting wholly or partly of PNA are, in effect, capable of displacing the strand complementary to the strand with which they can hybridize; see Nielsen, P. E. et al., Science 254, 1497–1500 (1991).

The actual transcription is effected under the usual conditions, which are well known, in the presence of the appropriate RNA polymerase and of ribonucleoside triphosphates, and these conditions will not be restated here.

The present invention also enables a differential transcription of two different sequences to be effected in the same reaction medium containing an RNA polymerase recognizing the modified promoter. Among the modified promoters according to the invention, some enable a level of transcription to be obtained which is equal to that obtained using a wild-type promoter, and others, on the contrary, enable a lower level of transcription to be obtained. Differential transcription has numerous uses. In particular, it permits:

(1) the transcription of the coding and non-coding strands of a template which carries a modified promoter at each end or at only one end. The introduction of a difference in the efficiency of the two promoters makes it possible, furthermore, to obtain a synthesis of larger amounts of one strand with respect to the other, if the two strands initially have the same capacity for transcription with the same promoter. In the case where, on the contrary, the two strands do not have the same efficiency of transcription with the same promoter, the choice of two promoters differing in efficiency enables the level of transcription of the two transcripts to be balanced;

(2) the simultaneous expression of proteins or polypeptides which it is desired to obtain in certain proportions within the reaction medium, such as, for example, two subunits a and b of the same holoenzyme $a_2b$. To this end, the sequence of subunit a is placed under the control of a wild-type promoter, and the sequence b is placed under the control of a modified promoter whose efficiency is half that of the wild-type promoter.

BRIEF DESCRIPTION OF THE DRAWINGS

FIG. 1 is a comparative table of the consensus sequences of the promoters for T3, T7 and SP6 RNA polymerases.

FIGS. 3A–3C describe the set of combinations of promoter structures studied by transcription using T7 RNA polymerase. Grey-dotted bars represent the oligonucleotide structures used. For each hybrid, the upper bar corresponds to a sequence described (from left to right) from 5' to 3', and the lower bar to a sequence described from 3' to 5'. Hatched regions represent sites amputated on one or other of the strands, in accordance with FIG. 2. The level of production of the transcription products relating to a given size, the products being visualized by autoradiography, is indicated according to the following scheme: (−): absence of the transcription product; (*): very low level; (): low level; (*): moderate level; (**): high level; (***): very high level. The signals boxed in rectangles correspond to the transcription products of expected size with respect to the presumed start site, and the encircled signals correspond to a transcription product identical in size to the non-template (upper) strand of the hybrids studied.

FIG. 4A describes combinations of promoter sequences studied by transcription using T7 RNA polymerase. Grey-dotted bars represent the oligonucleotide structures used. For each hybrid, the upper bar corresponds to a sequence described (from left to right) from 5' to 3', and the lower bar to a sequence described from 3' to 5'. Hatched regions represent sites amputated on one or other of the strands, in accordance with FIG. 2. The level of production of the transcription products relating to a given size, the products being visualized by autoradiography, is indicated as in FIGS. 3A–3C.

FIG. 5A describes combinations of promoter sequences studied by transcription using T7 RNA polymerase, with the same conventions as for FIGS. 4A and 4B.

FIG. 7A shows a modified promoter structure created by hybridization of an oligonucleotide with the sequence of the HIV genome (pol gene). This oligonucleotide is composed of two flanking portions complementary to the target, and of a sequence identical to the consensus sequence of the promoter of phage T7 RNA polymerase (17 bases). The sequence identities are represented by rods (I), and the portion in bold type on a grey-dotted background represents the partially double-stranded structure corresponding to a "hemipromoter" structure.

EXAMPLES

The examples which follow illustrate the invention.

Example 1

Analysis of the Functionality of Modified Promoters

Different structures of promoters of (DNA-dependant) phage RNA polymerases, and more especially of phage T7, were studied. These structures are obtained by the combination of different oligodeoxynucleotide sequences synthesized chemically with an Applied Biosystems 394 DNA/RNA Synthesizer apparatus. The listing of these sequences (SEQ ID NO:1 to SEQ ID NO:8) is appended.

The preparation of the DNA templates studied was carried out from solutions containing $2.5 \times 10^{14}$ copies of oligodeoxynucleotides (ODN). The different solutions needed for constructing the template are combined in a microcentrifuge tube and then dried under vacuum. The mixture is taken up in 10 $\mu$l of 50 mM Tris-HCl buffer (pH 7.5) and resuspended. Hybridization of structures possessing an at least partial sequence complementarity is carried out by denaturation at 95° C. for 5 minutes, centrifugation (14,000×g, 10 seconds) and then a lowering to room temperature for 10 minutes. At this stage, the templates may be used or stored at −20° C. Transcription tests are carried out using 2 $\mu$l of a 1/10 dilution of the above solutions, equivalent to $5 \times 10^{12}$ copies of the single- or double-stranded template.

Transcription reactions are carried out in the following buffer: 40 mM Tris-HCl (pH 8.1), 1 mM spermidine, 5 mM dithiothreitol (DTT), 0.01% Triton X-100, polyethylene glycol (PEG, molecular weight 4000) 80 mg/ml, bovine serum albumin (BSA) 50 $\mu$g (Boehringer). The final reaction volume is 20 $\mu$l and contains ATP, CTP, GTP, UTP (4 mM each), 5 $\mu$Ci of [$\alpha$-$^{32}$P]UTP, 20 mM MgCl$_2$, 5 Units of T7 RNA polymerase (New England Biolabs) and 12 Units of RNA Guard (Pharmacia). Incubation is carried out at 37° C. for 2 hours.

A 5 $\mu$l fraction of the reaction mixture is withdrawn and mixed with 5 $\mu$l of the following solution: 98% formamide, 0.083% xylene cyanole, 0.083% bromophenol blue, 10 mM EDTA pH 5.0. The samples are heated to 65° C. for 5 minutes and then cooled rapidly on ice. They are analysed by electrophoresis (2 hours, 150 volts) on 12–15% polyacrylamide gel, 7M urea. The gels are then treated for 20 minutes in an acetic acid/methanol (10:20, %/%) solution, dried under vacuum and autoradiographed for 12 hours at −80° C.

Figure 2:
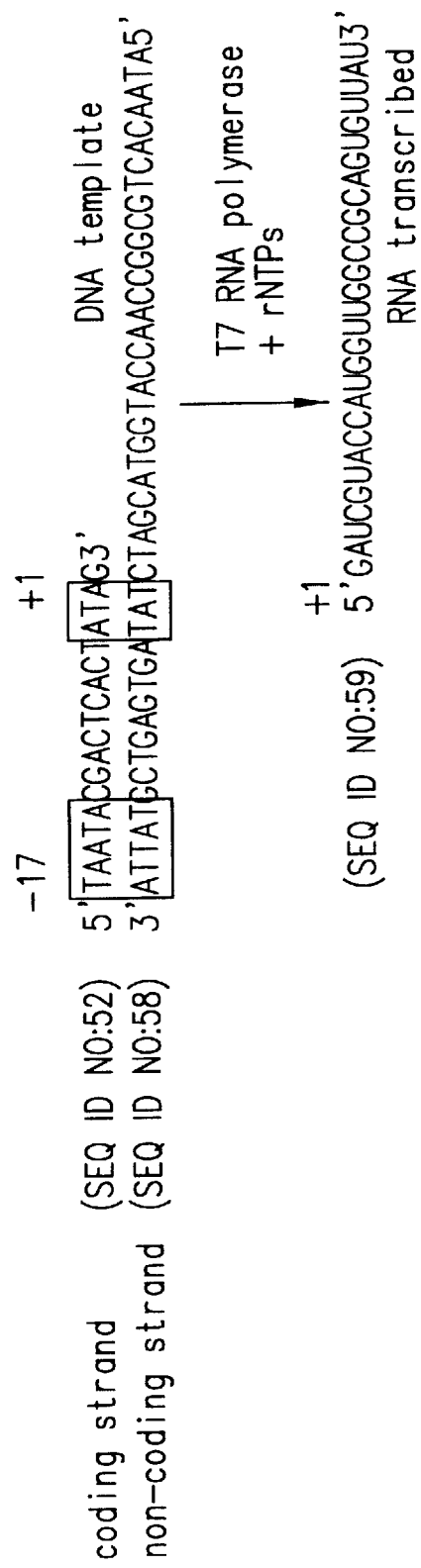
FIG. 2 shows the consensus (double-stranded) sequence of the T7 RNA polymerase promoter between positions −17 and +1. The normal transcription product is shown. The transcription start site is indicated by the symbol +1. The boxed areas define the sites on which deletions have been carried out, on the non-template strand (upper strand) and/or on the template (lower) strand, in accordance with Example 1.
Figure 3A:
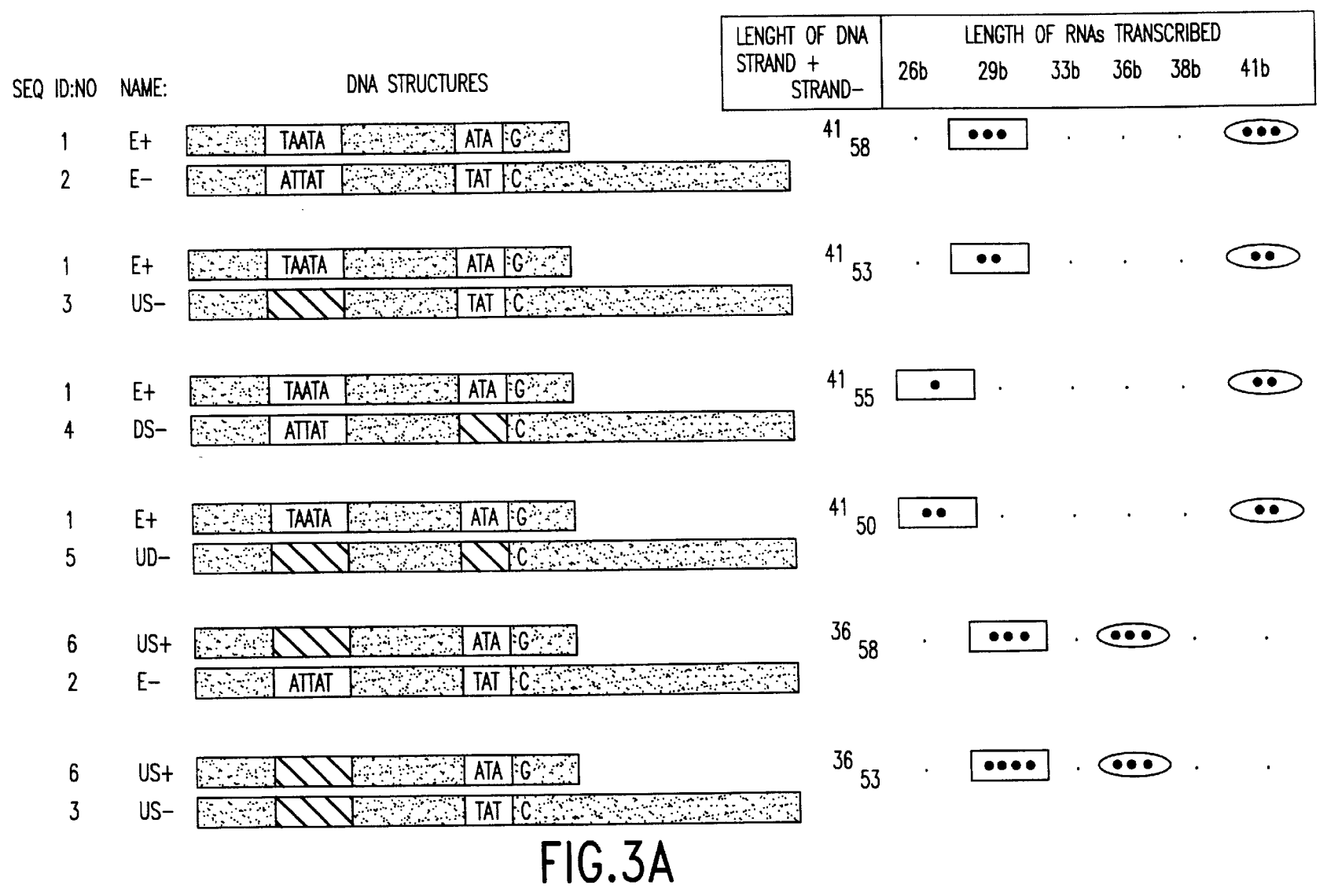
Figure 3B:
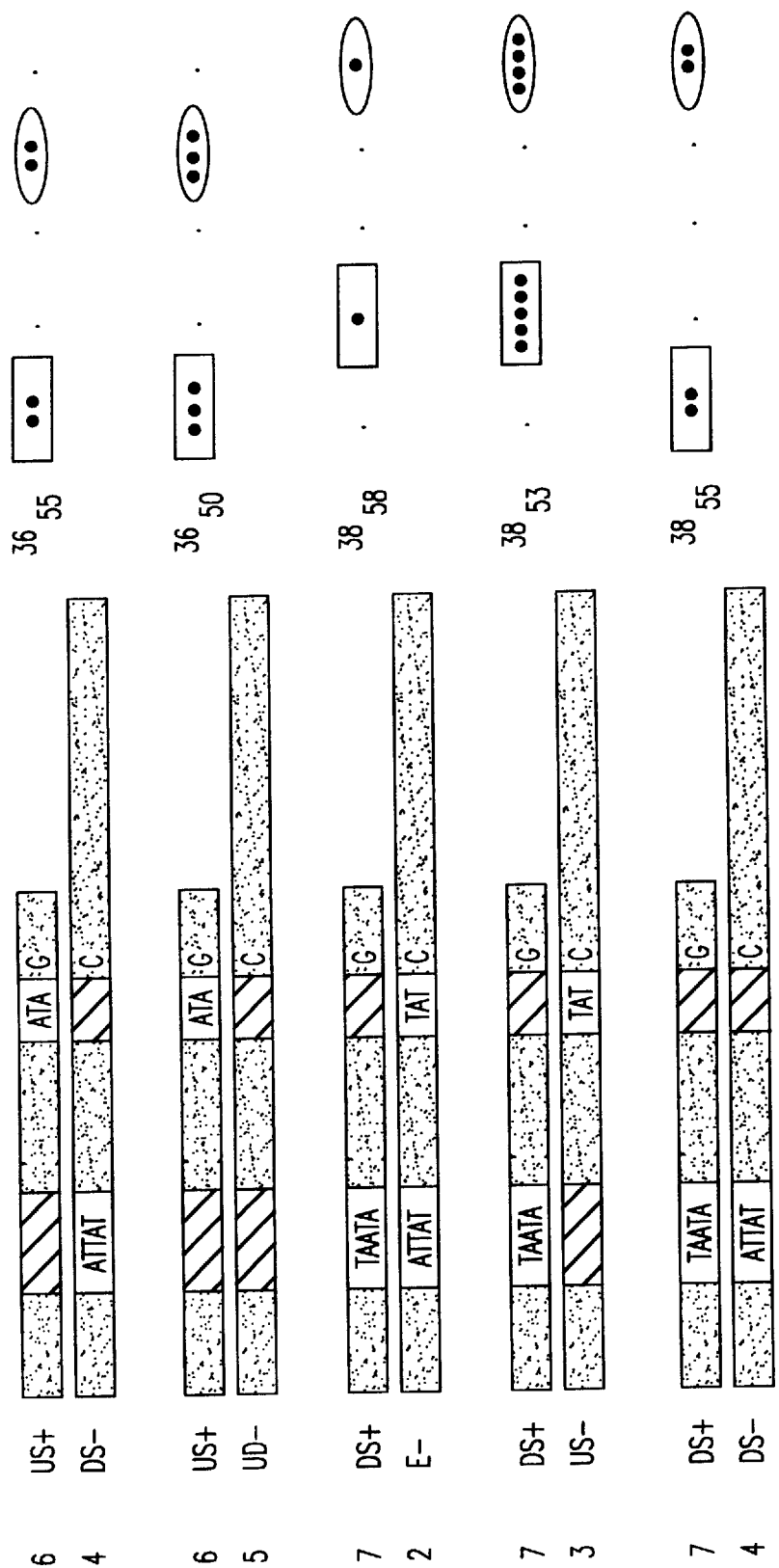
Figure 3C:
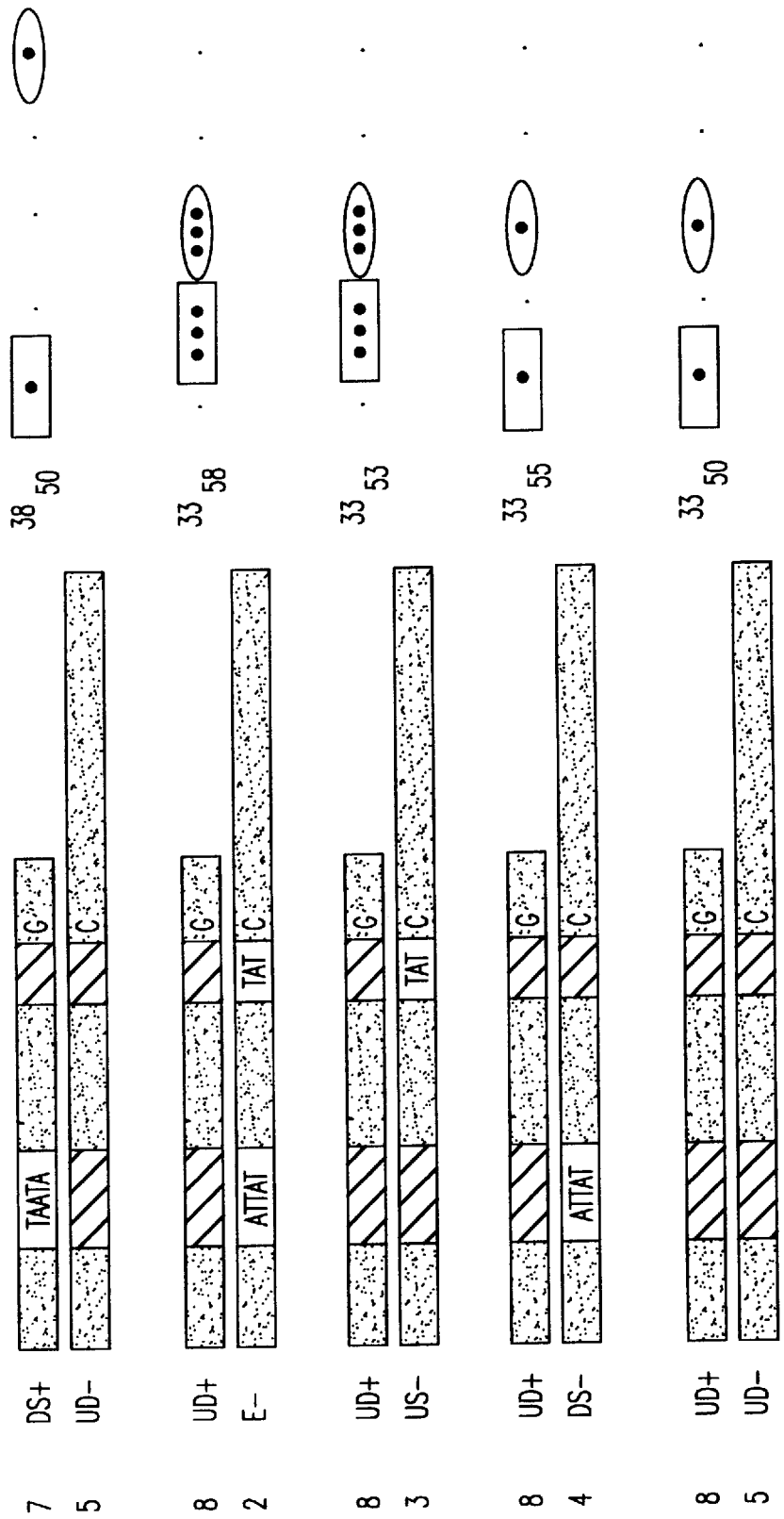

The different combinations studied make it possible to determine the influence of deletions located in the upstream (US) and downstream (DS) regions of the consensus sequence of the promoter of phage T7 RNA polymerase on the efficiency of transcription of a defined DNA template. The combinations also make it possible to determine the respective influence of each of these deletions depending on whether they are located on the non-template or the template strand of the double-stranded promoter (FIG. 2). The various combinations studied in this example are shown diagrammatically in FIGS. 3A–3C.

Comparative analysis of the results arising from the combinations SEQ ID NO:1/SEQ ID NO:2, SEQ ID NO:1/SEQ ID NO:3, SEQ ID NO:6/SEQ ID NO:2 and SEQ ID NO:6/SEQ ID NO:3 (FIG. 3A) enables the influence of deletions upstream of the core (−4 to −12) of the promoter to be determined. It shows in this case that a deletion on the non-template strand has, on its own, little effect, but that a deletion on the template strand on its own reduces the activity of the promoter. However, a double deletion (non-template and template strand) reestablishes a normal level of transcription, showing that the upstream portion of the promoter can be replaced by any double-stranded sequence without modifying the activity of this promoter. The promoter of phage T7 RNA polymerase can hence be modified upstream of position −12 without affecting the transcription yield or modifying the transcription start site.

Comparative analysis of the results arising from the combinations SEQ ID NO:1/SEQ ID NO:2, SEQ ID NO:1/

SEQ ID NO:4, SEQ ID NO:7/SEQ ID NO:2 and SEQ ID NO:7/SEQ ID NO:4 (FIGS. 3A and 3B) enables the influence of deletions downstream of the core (positions −4 to 12) of the promoter to be determined. Deletion of the promoter downstream induces a shifting of the transcription start site relative to the site of the wild-type promoter (C, corresponding to position +1). In effect, a smaller-sized transcript (26 instead of 29 nucleotides) is observed in all cases where a promoter comprises a downstream deletion on the template strand. This demonstrates that the positioning of the T7 RNA polymerase on the core of the promoter imposes the localization of the transcription start site on the template strand. The downstream portion of the promoter (−1 to −3) may hence be removed and replaced by a sequence different from that defined in the overall consensus of 17 base pairs, demonstrating that a promoter thus modified retains its functionality, even if the reaction yield is slightly lower.

Comparative analysis of the results arising from the combinations SEQ ID NO:1/SEQ ID NO:2, SEQ ID NO:1/SEQ ID NO:3, SEQ ID NO:1/SEQ ID NO:4 and SEQ ID NO:1/SEQ ID NO:5 (FIG. 3A) enables the influence of deletions to be determined in relation to their respective localization on the template strand of the promoter. A deletion located upstream does not modify the size of the transcript, but slightly lessens the efficiency of transcription relative to the wild-type promoter. On the other hand, a deletion located downstream results in a shorter transcription product being obtained (shifting of the transcription start site), and affects the efficiency of transcription by more than 50%. Double deletion (upstream and downstream) produces a shorter transcript, but its efficiency of transcription is similar to that corresponding to the deletion located downstream. In other words, there is not a cumulative effect of the two types of deletion.

Comparative analysis of the results arising from the combinations SEQ ID NO:1/SEQ ID NO:2, SEQ ID NO:6/SEQ ID NO:2, SEQ ID NO:7/SEQ ID NO:2 and SEQ ID NO:8/SEQ ID NO:2 (FIGS. 3A–3C) enables the influence of deletions on the non-template strand of the promoter to be determined. A deletion located upstream does not modify the efficiency of transcription relative to the wild-type promoter. On the other hand, a deletion located downstream reduces the efficiency of transcription by more than 50%. The effect of both mutations is not cumulative, since a double deletion (upstream and downstream) enables a transcription to be obtained which is almost as strong as the control.

Comparative analysis of the results arising from the combinations SEQ ID NO:1/SEQ ID NO:2, SEQ ID NO:6/SEQ ID NO:4, SEQ ID NO:6/SEQ ID NO:5, SEQ ID NO:8/SEQ ID NO:4, SEQ ID NO:7/SEQ ID NO:3, SEQ ID NO:8/SEQ ID NO:3, SEQ ID NO:7/SEQ ID NO:5, SEQ ID NO:6/SEQ ID NO:3, SEQ ID NO:7/SEQ ID NO:4 and SEQ ID NO:8/SEQ ID NO:5 (FIGS. 3A–3C) enables the functionality of promoter structures possessing at least one deletion on each strand (non-template and template) to be studied. It enables it to be established that a homoduplex promoter lacking its upstream portion (on both strands) and also a promoter lacking its downstream portion (on both strands) retain good functionality relative to the wild-type promoter. Similarly, any promoter lacking its downstream portion on the template strand (but not lacking it on the non-template strand) is functional. This demonstrates that it is possible to define a modified promoter for phage RNA polymerase on the basis of a minimum sequence present in a target DNA. Lastly, even though the efficiency of a doubly amputated (upstream and downstream on both strands) homoduplex promoter is reduced relative to the wild-type promoter, it should be noted that this type of minimum structure nevertheless enables transcripts to be obtained with a not insignificant efficiency.

Under similar conditions, it is possible to show that the template strand of the promoter enables, in single-stranded form, a transcript to be obtained which is identical in size to that obtained using a double-stranded promoter. A template single-stranded sequence of a promoter hence possesses the information needed for binding phage T7 RNA polymerase and initiating transcription.

In summary, the shortened homo- or heteroduplex double-stranded promoters retain great functionality relative to the wild-type promoter. In particular, a deletion on both strands upstream has no influence on the transcription yield. A deletion downstream on the template strand has little effect on the transcription yield, but simply modifies the size of the transcript by shifting the transcription start site on the template. Retention of the downstream portion on the non-template strand alone of the promoter (localization −3 to −1), at the $^{5'}TATA^{3'}$ sequence, enables an efficiency of transcription to be retained which is close to that obtained using the wild-type promoter. Nevertheless, it is clearly apparent from these data that it is possible to obtain smaller-sized modified promoters enabling transcription to be initiated from a given site.

Example 2

Figure 4A:
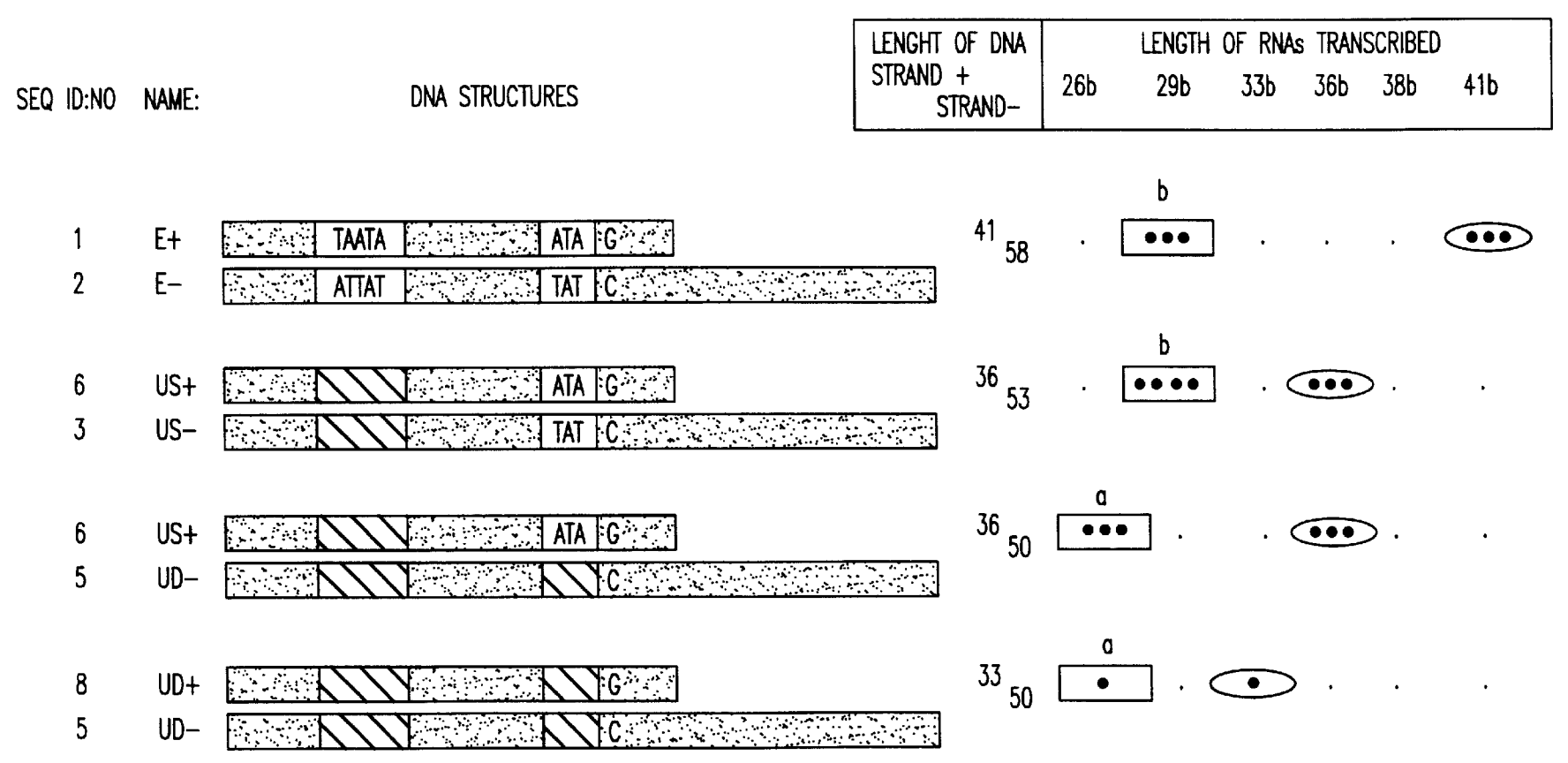
Figure 4B:
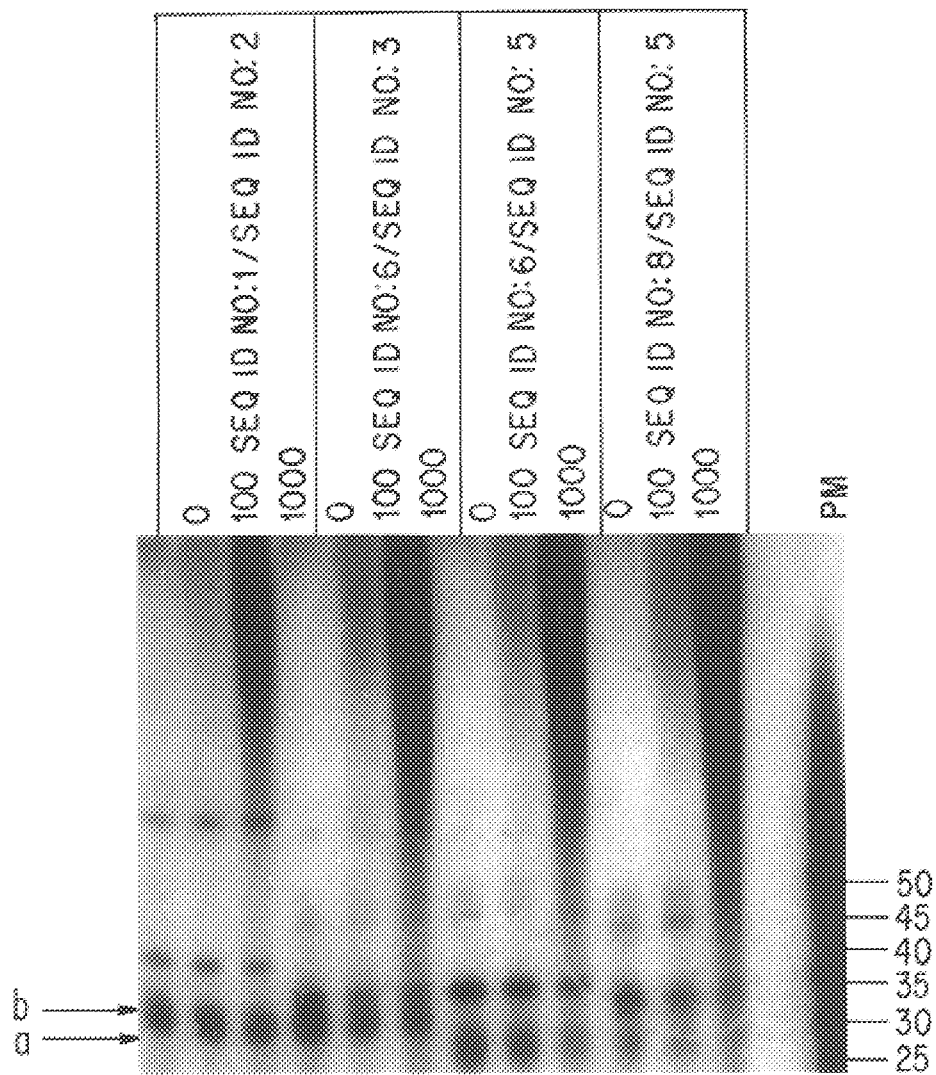
FIG. 4B shows the autoradiograph obtained at the end of the experiments illustrated diagrammatically in FIG. 4A. The specifically expected transcription signals are indicated by arrows (a: 26 nucleotides; b: 29 nucleotides), in accordance with FIG. 4A. The figures above each lane indicate the amount of exogenous DNA used in the test in question. The sizes of the molecular weight (MW) markers appear at the right-hand side of the autoradiogram.

Qualitative Analysis of the Specificity of Transcription From Modified Promoters In accordance with Example 1, the specificity of in vitro transcription of modified promoters was studied in the presence of exogenous salmon sperm DNA at different concentrations per test. The combinations SEQ ID NO:1/SEQ ID NO:2, SEQ ID NO:6/SEQ ID NO:3, SEQ ID NO:6/SEQ ID NO:5 and SEQ ID NO:8/SEQ ID NO:5 were studied in the presence of 0, 10, 100 and 1000 ng of exogenous DNA (FIGS. 4A and 4B) . This study enables it to be demonstrated, in a few special cases chosen from Example 1, that transcription effected in vitro is intrinsically linked to the presence of a functional promoter structure, and not to the presence of a random DNA sequence available for the T7 RNA polymerase. The experimental tests were carried out in a manner identical to those of Example 1.

The presence of a high concentration (1000 ng/test) of exogenous DNA leads to a strong background, corresponding to large-sized non-specific transcripts (FIG. 4B). Nevertheless, the efficiency of transcription of the specific target is not modified quantitatively in the presence or absence of exogenous DNA. This demonstrates that the promoter structures studied permit a preferential and efficient binding of the T7 RNA polymerase, leading to the specific transcription of a target lacking a promoter. This observation is in agreement with the fact that the intensity of the non-specific background is inversely proportional to the efficiency of the promoter present, that is to say the relative intensity of the product of expected size. These findings hence demonstrate the functionality of the modified promoters which permit a specific transcription of a target located downstream.

Example 3

Figure 5B:
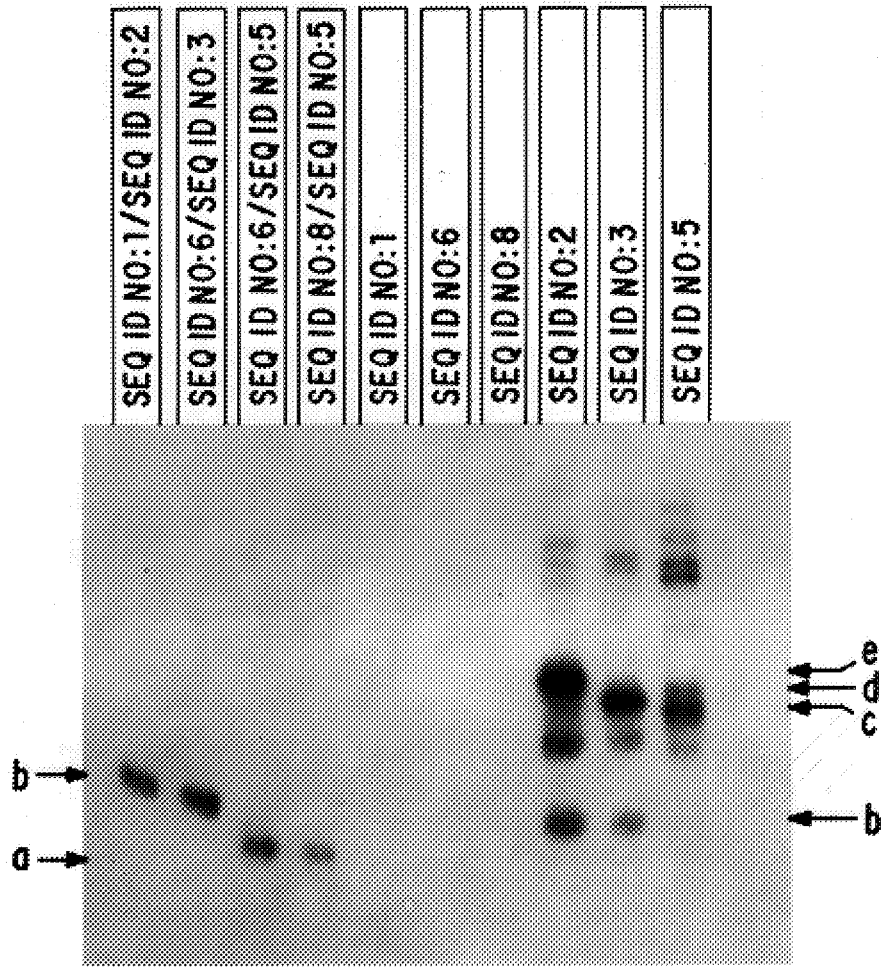
FIG. 5B shows the autoradiograph obtained at the end of the experiments illustrated diagrammatically in FIG. 5A. The specifically expected transcription signals are indicated by arrows (a: 26 nucleotides; b: 29 nucleotides; c: 50 nucleotides; d: 53 nucleotides; e: 58 nucleotides), in accordance with FIG. 5A.

Qualitative Analysis of the RNAs Transcribed From A Target Sequence Controlled by A Modified Promoter The qualitative analysis of the relative efficiency of different types of promoter structures was complemented by a specific detection of the transcribed RNAs corresponding to the sequence located downstream of the promoter structure. To this end, transcriptional tests were carried out in accordance with Example 1, except for any incorporation of modified nucleotides. The combinations SEQ ID NO:1/SEQ ID NO:2, SEQ ID NO:6/SEQ ID NO:3, SEQ ID NO:6/SEQ ID NO:5, SEQ ID NO:8/SEQ ID NO:5, SEQ ID NO:1, SEQ ID NO:6, SEQ ID NO:8, SEQ ID NO:2, SEQ ID NO:3 and SEQ ID NO:5 were studied. Following the actual transcription reaction in the absence of isotope, the samples are loaded onto an electrophoresis gel. After migration according to the conditions of Example 1, the nucleic acids are transferred electrically onto a nylon membrane (Hybond N, Amersham) using an apparatus (Biorad) in a TBE×0.5 buffer for two hours at 80 volts. The membranes are dried for 10 minutes at 80° C., and the nucleic acids are then bound to the membrane by UV irradiation using a Stratalinker apparatus (Stratagene). The membranes are prehybridized at 42° C. in a prehybridization solution. Hybridization is carried out with an oligonucleotide probe (SEQ ID NO:9) radioactively labelled at its 3' end with [$\alpha$-$^{32}$P]ddATP in the presence of terminal transferase, and purified. Hybridization is carried out for 12 hours under discriminating ("stringent") conditions not permitting non-specific hybridizations, and washes are also carried out stringently. The membrane is then wrapped in a cellophane film and autoradiographed for 24 hours at −80° C. The results obtained are presented in FIG. 5. They show clearly that a double-stranded promoter shortened upstream (SEQ ID NO:6/SEQ ID NO:3) is as effective as a wild-type promoter (SEQ ID NO:1/SEQ ID NO:2). Similarly, a promoter shortened upstream on the non-template strand and upstream and downstream on the template strand (SEQ ID NO:6/SEQ ID NO:5) enables a specific transcript to be obtained, that is to say one complementary to the detection probe for the target RNA. The yield obtained from this transcript is similar to that obtained using the wild-type promoter, confirming the efficiency of this modified promoter for the transcription of an RNA complementary to the template located downstream of the promoter. The RNA produced under these conditions possesses a size reduced by 3 nucleotides relative to the RNA originating from the wild-type promoter. This is due to the shifting of the transcription start site on the template strand, owing to the downstream deletion on the latter. This shifting probably amputates the first three bases from the transcribed RNA, but does not modify the sequence located downstream, since a hybridization signal of the same intensity as in the case of the wild-type promoter is obtained with the probe specific for the expected transcript. A transcript reduced in size by 3 nucleotides is also obtained from the double-stranded promoter amputated upstream and downstream (SEQ ID NO:8/ SEQ ID NO:5). As expected, the strands corresponding to the non-template strand of the promoter (SEQ ID NO:1, SEQ ID NO:6, SEQ ID NO:8) do not enable specific transcripts to be obtained. On the other hand, with the template strand alone, wild-type or amputated upstream (SEQ ID NO:2 and SEQ ID NO:3, respectively), a specific transcript of the expected size (29 nucleotides) is obtained. This demonstrates for the first time the capacity of template strands of phage promoters to initiate a transcription at a precise site. A template strand of a doubly amputated promoter (SEQ ID NO:5) does not enable transcription to be initiated, showing the importance of the $^{5'}$TAT$^{3'}$ sequence located in the downstream portion of the consensus sequence of the T7 promoter. Transcription capacity may be reestablished by hybridization in trans of a non-template strand of the promoter containing at least this downstream sequence of the promoter. It is important to note that these single-stranded (template strand) promoters all result in initiations of transcription at other sites than those defined by the positioning of the RNA polymerase on its wild-type promoter. In particular, transcripts containing the expected RNA sequence, but equal in length to that of the template strand, are obtained. This results from the initiation of a transcription from the free 3' end of an oligonucleotide, as demonstrated previously; see Schenborn, E. T. and Mierendorf, R. C. Jr., Nucleic Acid Research, 13, 6223–6236 (1985).

In conclusion, phage promoters amputated upstream and downstream of their consensus sequence, single-stranded or double-stranded, prove capable of specifically inducing transcription at a particular site.

Figure 6:
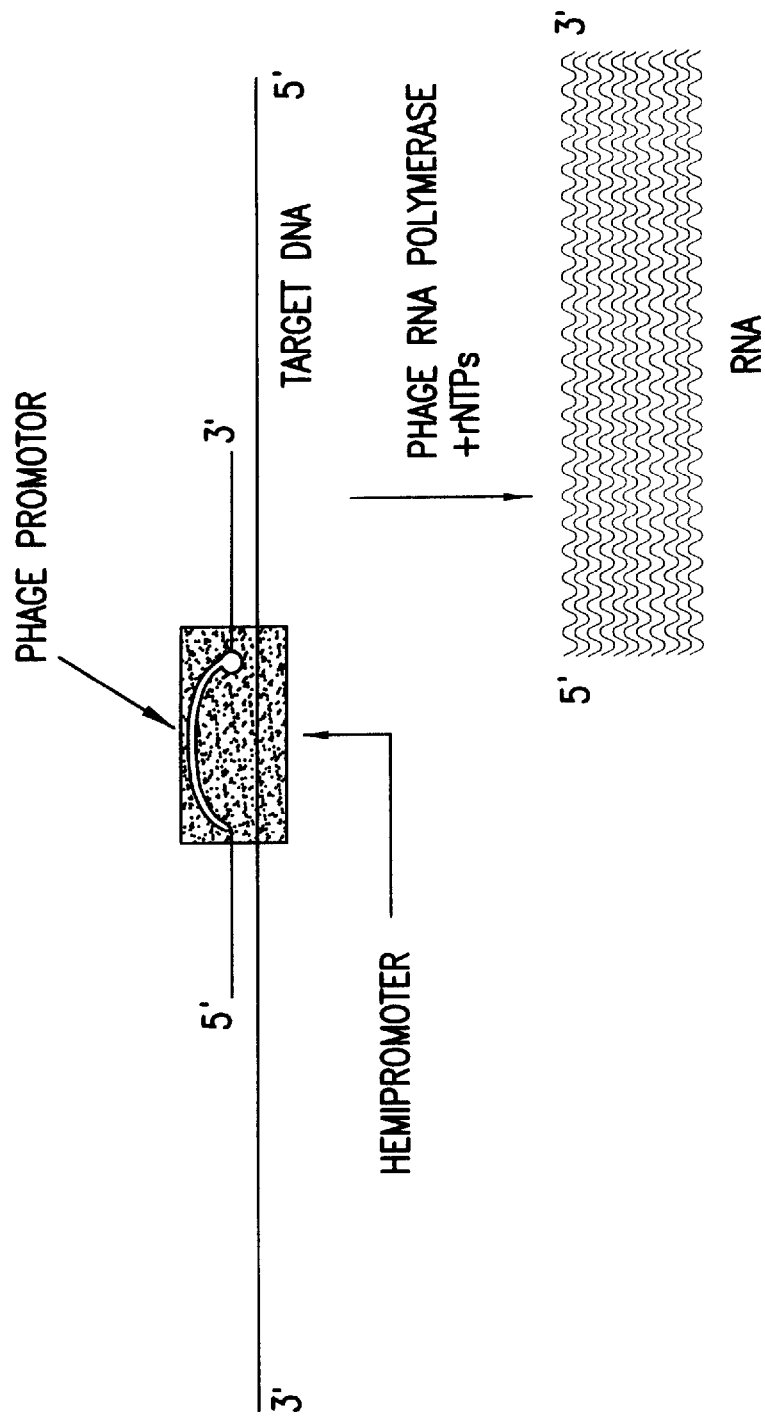
FIG. 6 describes diagrammatically the functioning of a modified promoter according to the invention, with the installation of a modified promoter sequence (non-template strand; emboldened line) on some or other site of a target sequence in order to define a specific transcription start site. The sequence shown as an emboldened line is maintained on the target sequence by the hybridization of flanking sequences complementary to the target sequence. The promoter region, to which the RNA polymerase is bound, is represented by a grey-dotted rectangle. The RNAs obtained by transcription in the presence of ribonucleotide triphosphates (rNTPs) are represented by wavy lines. The transcription start site is designated by a black circle.

Thus, according to the invention, and as shown in the experimental part above, it is possible to create structures of modified or partially retained phage promoters. These structures may be produced, in particular, by hybridization of an oligonucleotide composed successively (from 5' to 3') of a region complementary to the single-stranded target (flanking region), a sequence of the promoter non-template strand of the phage RNA polymerase and optionally a second flanking region complementary to the target (FIG. 6). Such an oligonucleotide can play the part of a hemipromoter (promoter non-template strand) for transcription by means of RNA polymerase. Depending on the nature of the target sequence opposite to the sequence of the promoter (in the target-promoter duplex), and in order to limit the effect of mispairings of this region on the RNA polymerase binding capacity, modified bases (for example inosine) may be introduced into particular positions of the sequence of the promoter. These modifications must be suited to each particular case of target sequence in order to enhance the binding of the RNA polymerase to the "hemipromoter" structure. The notion of "hemipromoter" covers the idea of a recognition of an imperfectly paired promoter sequence. The RNA polymerase binds to the hemipromoter structure and effects the transcription of RNAs whose 5' end (generally a G) corresponds to the first base located downstream of the hemipromoter structure (FIG. 6). Any method of installation of this type of "hemipromoter" structure, and also the use of such a structure, form part of the invention.

The possible step of initial denaturation of a double-stranded nucleic acid to be transcribed may be performed thermally, chemically or enzymatically.

Figure 7B:
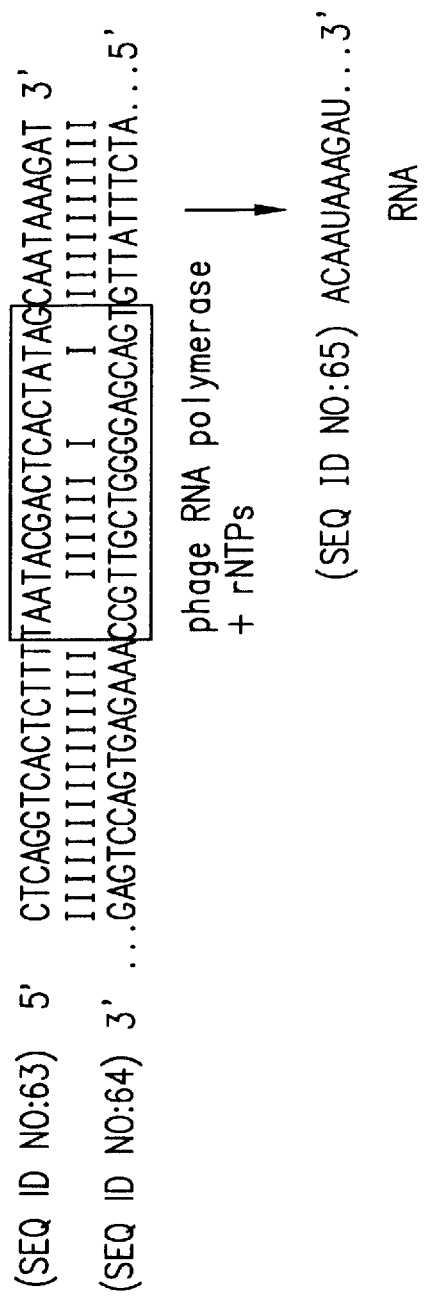
FIG. 7B shows a modified promoter structure created by hybridization of an oligonucleotide with the sequence of the HIV genome (gag gene). This oligonucleotide is composed of two flanking portions complementary to the target, and of a sequence identical to the consensus sequence of the promoter of phage T7 RNA polymerase (17 bases). The sequence identities are represented by rods (I), and the portion in bold type on a grey-dotted background represents the partially double-stranded structure corresponding to a "hemipromoter" structure. The RNAs transcribed in the presence of T7 RNA polymerase and ribonucleotides (rNTPs) are shown. Suspension points symbolize one end of a nucleic acid which can be of an indefinite length.

It is an easy matter to find, within a target sequence, regions having sufficient homology with the consensus sequence of a phage RNA polymerase promoter, and all the more so with a shortened sequence, sufficient to initiate transcription, as shown above, in order to create a "hemi-promoter" structure by hybridization with a target strand of a core promoter sequence flanked by at least one sequence specific for the target. The genome of the human immunodeficiency virus (HIV) possesses, for example, two regions of significant homology with the consensus sequence of the promoter of phage T7 RNA polymerase ($^{5'}$TAATACGACTCACTATAG$^{3'}$) (SEQ ID NO:52). These sequences are $^{5'}$GGCAACGACCCCTCGTCA$^{3'}$ (SEQ ID NO:53) and $^{5'}$TAATACGACTCACAATAT$^{3'}$ (SEQ ID NO:54), and are located, respectively, within the gag and pol genes. The bases in bold type are identical in the consensus sequence of the promoter and in the sequences determined by seeking optimal alignments between the said consensus sequence and the total sequence of the HIV genome. Hybridization of a sequence containing a portion of the consensus sequence (non-template strand) of the promoter of phage T7 RNA polymerase, flanked by sequences complementary to the HIV target, enables a "hemipromoter" structure to be installed on the HIV genome, and a specific transcription to be effected, in the presence of T7 RNA polymerase and ribonucleoside triphosphates (rNTPs), from the site thus defined (FIGS. 7A and 7B). This example consequently illustrates the possibility of application of this method of initiation of transcription from a nucleic acid sequence of interest, potentially to all existing biological systems.

What is claimed is:

1. An oligonucleotide that serves as a promoter non-template strand in transcription of a sequence of a nucleotide target, in the presence of a phage RNA polymerase, from a site of the target which is not normally a transcription start site for the phage RNA polymerase, said polymerase having a specific natural promoter comprising a consensus sequence at least from position −17 to position −1, wherein:

said oligonucleotide comprises a core sequence flanked on at least one of its ends by a nucleotide sequence capable of hybridization with a sequence of the target, said core sequence consists of a sequence of 6 to 9 consecutive nucleotides chosen from the region −12 to −4 of the non-template strand of the specific natural promoter, or a sufficiently homologous sequence to enable the functionality of the RNA polymerase to be retained, at least a first flanking sequence is complementary to a first region of the target, and a second flanking sequence, when present, is complementary to a second region of the target, said first and second regions being separated on the target by a sequence having a number of nucleotides equal to the number of nucleotides in the core sequence, and the number of nucleotides in the flanking sequence, or the sum of the number of nucleotides in the flanking sequences, is at least sufficiently high to enable the oligonucleotide to hybridize with the target at a temperature of use of the RNA polymerase.

2. An oligonucleotide according to claim 1, wherein said oligonucleotide contains an upstream flanking sequence in which the number of nucleotides is such that the sum of the numbers of nucleotides in the core sequence and in the upstream flanking sequence is equal to at least 10.

3. An oligonucleotide according to claim 1, wherein the flanking sequences each contain from 5 to 12 nucleotides.

4. An oligonucleotide according to claim 2, wherein the flanking regions each contain from 5 to 12 nucleotides.

5. An oligonucleotide according to claim 1, wherein said oligonucleotide contains an upstream flanking sequence in which the number of nucleotides is such that the sum of the numbers of nucleotides in the core sequence and in the upstream flanking sequence is equal to at least 11.

6. An oligonucleotide according to claim 1, wherein the sequence −12 to −4 of the non-template strand of the promoter is selected from the group consisting of:
ACCCTCACT (SEO ID NO: 45),
GGTGACACT (SEO ID NO: 46),
CGACTCACT (SEQ ID NO: 47),
GGGCACACT (SEO ID NO: 48),
CAACTCACT (SEO ID NO: 49),
CGACTCAGT (SEO ID NO: 50), and
GAACTCACT (SEO ID NO: 51).

7. An oligonucleotide according to claim 2, wherein the sequence −12 to −4 of the non-template strand of the promoter is selected from the group consisting of:
ACCCTCACT (SEO ID NO: 45),
GGTGACACT (SEO ID NO: 46),
CGACTCACT (SEQ ID NO: 47),
GGGCACACT (SEO ID NO: 48),
CAACTCACT (SEO ID NO: 49),
CGACTCAGT (SEO ID NO: 50), and
GAACTCACT (SEO ID NO: 51).

8. An oligonucleotide according to claim 3, wherein the sequence −12 to −4 of the said non-template strand of the said promoter is selected from the group consisting of:
ACCCTCACT (SEO ID NO: 45),
GGTGACACT (SEO ID NO: 46),
CGACTCACT (SEQ ID NO: 47),
GGGCACACT (SEO ID NO: 48),
CAACTCACT (SEO ID NO: 49),
CGACTCAGT (SEO ID NO: 50), and
GAACTCACT (SEO ID NO: 51).

9. A method of transcribing a nucleotide target sequence using an oligonucleotide as defined in claim 1, comprising hybridizing the at least one flanking sequence of the oligonucleotide with the target in the presence of an RNA polymerase, and transcribing a sequence of the target from said site which is not normally a transcription start site for the RNA polymerase.

10. A method according to claim 9, wherein said oligonucleotide contains an upstream flanking sequence in which the number of nucleotides is such that the sum of the number of nucleotides in the core sequence and in the upstream flanking sequence is equal to at least 10.

11. A method according to claim 9, wherein the flanking sequences each contain from 5 to 12 nucleotides.

12. A method according to claim 9, wherein the sequence −12 to −4 of the non-template strand of the promoter is selected from the group consisting of:
ACCCTCACT (SEO ID NO: 45),
GGTGACACT (SEO ID NO: 46),
CGACTCACT (SEQ ID NO: 47),
GGGCACACT (SEO ID NO: 48),
CAACTCACT (SEO ID NO: 49),
CGACTCAGT (SEO ID NO: 50), and
GAACTCACT (SEO ID NO: 51).

13. A method for preparing oligonucleotides that serve as promoter non-template strands in transcription of a sequence of a nucleotide target, in the presence of a phase RNA polymerase, from a site which is not normally a transcription start site for the phage RNA polymerase, said polymerase having a specific natural promoter comprising a consensus sequence at least from position −17 to position −1, comprising:

(1) synthesizing oligonucleotides comprising a core sequence flanked on at least one of its ends by a nucleotide sequence capable of hybridization with a sequence of the target, wherein
- said core sequence consists of a sequence of 6 to 9 consecutive nucleotides chosen from the region −12 to −4 of the non-template strand of the specific natural promoter, or a sufficiently homologous sequence to enable the functionality of the RNA polymerase to be retained,
- at least a first flanking sequence is complementary to a first region of the target, and a second flanking sequence, when present, is complementary to a second region of the target, said first and second regions being separated on the target by a sequence having a number of nucleotides equal to the number of nucleotides in the core sequence, and
- the number of nucleotides in the flanking sequence, or the sum of the number of nucleotides in the flanking sequences, is at least sufficiently high to enable the oligonucleotide to hybridize with the target at a temperature of use of the RNA polymerase, (2) performing tests of transcription of the target using the oligonucleotides obtained, and (3) eliminating oligonucleotides which do not enable transcription to be effected with a yield at least equal to a predetermined threshold, thereby preparing said oligonucleotides that serve as promoter non-template strands in transcription of a sequence of a nucleotide target, in the presence of a phase RNA polymerase, from a site which is not normally a transcription start site for the phage RNA polymerase.

14. A method according to claim 13, wherein said oligonucleotide contains an upstream flanking sequence in which the number of nucleotides is such that the sum of the number of nucleotides in the core sequence and in the upstream flanking sequence is equal to at least 10.

15. A method according to claim 13, wherein the flanking sequences each contain from 5 to 12 nucleotides.

16. A method according to claim 13, wherein the sequence −12 to −4 of the non-template strand of the promoter is selected from the group consisting of:

ACCCTCACT (SEO ID NO: 45),
GGTGACACT (SEO ID NO: 46),
CGACTCACT (SEQ ID NO: 47),
GGGCACACT (SEO ID NO: 48),
CAACTCACT (SEO ID NO: 49),
CGACTCAGT (SEO ID NO: 50), and
GAACTCACT (SEO ID NO: 51).

* * * * *

SEQUENCE LISTING ( 1 ) GENERAL INFORMATION:

( i i i ) NUMBER OF SEQUENCES: 65

( 2 ) INFORMATION FOR SEQ ID NO:1:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:1:

GATCGTACCA TGTAATACGA CTCACTATAG ATCGTACCAT G        41

( 2 ) INFORMATION FOR SEQ ID NO:2:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:2:

ATAACACTGC GGCCAACCAT GGTACGATCT ATAGTGAGTC GTATTACATG GTACGATC        58

( 2 ) INFORMATION FOR SEQ ID NO:3:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:3:

ATAACACTGC GGCCAACCAT GGTACGATCT ATAGTGAGTC GCATGGTACG ATC        53

( 2 ) INFORMATION FOR SEQ ID NO:4:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:4:

ATAACACTGC GGCCAACCAT GGTACGATCA GTGAGTCGTA TTACATGGTA CGATC        55

( 2 ) INFORMATION FOR SEQ ID NO:5:

( i ) SEQUENCE CHARACTERISTICS:
   ( A ) LENGTH: 50 base pairs
   ( B ) TYPE: nucleic acid
   ( C ) STRANDEDNESS: single
   ( D ) TOPOLOGY: linear ( i i ) MOLECULE TYPE: other nucleic acid
   ( A ) DESCRIPTION: /desc = "DNA"

( x i ) SEQUENCE DESCRIPTION: SEQ ID NO:5:

ATAACACTGC GGCCAACCAT GGTACGATCA GTGAGTCGCA TGGTACGATC  50

( 2 ) INFORMATION FOR SEQ ID NO:6:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "DNA"

( x i ) SEQUENCE DESCRIPTION: SEQ ID NO:6:

GATCGTACCA TGCGACTCAC TATAGATCGT ACCATG  36

( 2 ) INFORMATION FOR SEQ ID NO:7:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "DNA"

( x i ) SEQUENCE DESCRIPTION: SEQ ID NO:7:

GATCGTACCA TGTAATACGA CTCACTGATC GTACCATG  38

( 2 ) INFORMATION FOR SEQ ID NO:8:

( i ) SEQUENCE CHARACTERISTICS:
      ( A ) LENGTH: 33 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "DNA"

( x i ) SEQUENCE DESCRIPTION: SEQ ID NO:8:

GATCGTACCA TGCGACTCAC TGATCGTACC ATG  33

( 2 ) INFORMATION FOR SEQ ID NO:9:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "DNA"

( x i ) SEQUENCE DESCRIPTION: SEQ ID NO:9:

ATAACACTGC GGCCAAC  17

( 2 ) INFORMATION FOR SEQ ID NO:10:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "DNA"

( x i ) SEQUENCE DESCRIPTION: SEQ ID NO:10:

TAATACGACT CACTATAGGG AGA 23

( 2 ) INFORMATION FOR SEQ ID NO:11:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "DNA"

( x i ) SEQUENCE DESCRIPTION: SEQ ID NO:11:

TTGTCTTTAT TAATACAACT CACTATAAGG AGAGA 35

( 2 ) INFORMATION FOR SEQ ID NO:12:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "DNA"

( x i ) SEQUENCE DESCRIPTION: SEQ ID NO:12:

AACGCCAAAT CAATACGACT CACTATAGAG GGACA 35

( 2 ) INFORMATION FOR SEQ ID NO:13:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "DNA"

( x i ) SEQUENCE DESCRIPTION: SEQ ID NO:13:

TTCTTCCGGT TAATACGACT CACTATAGGA GGACC 35

( 2 ) INFORMATION FOR SEQ ID NO:14:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "DNA"

( x i ) SEQUENCE DESCRIPTION: SEQ ID NO:14:

GGACTGGAAG TAATACGACT CAGTATAGGG ACAAT 35

( 2 ) INFORMATION FOR SEQ ID NO:15:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "DNA"

( x i ) SEQUENCE DESCRIPTION: SEQ ID NO:15:

AGTTAACTGG TAATACGACT CACTAAAGGA GGTAC 35

( 2 ) INFORMATION FOR SEQ ID NO:16:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "DNA"

( x i ) SEQUENCE DESCRIPTION: SEQ ID NO:16:

TGGTCACGCT TAATACGACT CACTAAAGGA GACAC 35

( 2 ) INFORMATION FOR SEQ ID NO:17:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "DNA"

( x i ) SEQUENCE DESCRIPTION: SEQ ID NO:17:

AGCACCGAAG TAATACGACT CACTATTAGG GAAGA 35

( 2 ) INFORMATION FOR SEQ ID NO:18:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "DNA"

( x i ) SEQUENCE DESCRIPTION: SEQ ID NO:18:

CGTGGATAAT TAATTGAACT CACTATTAGG GAAGA 35

( 2 ) INFORMATION FOR SEQ ID NO:19:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "DNA"

( x i ) SEQUENCE DESCRIPTION: SEQ ID NO:19:

CCGACTGAGA CAATCCGACT CACTAAAGAG AGAGA 35

( 2 ) INFORMATION FOR SEQ ID NO:20:

( i ) SEQUENCE CHARACTERISTICS:
   ( A ) LENGTH: 35 base pairs
   ( B ) TYPE: nucleic acid
   ( C ) STRANDEDNESS: single
   ( D ) TOPOLOGY: linear ( i i ) MOLECULE TYPE: other nucleic acid
   ( A ) DESCRIPTION: /desc = "DNA"

( x i ) SEQUENCE DESCRIPTION: SEQ ID NO:20:

AGTCCCATTC TAATACGACT CACTAAAGGA GAGAC   35

( 2 ) INFORMATION FOR SEQ ID NO:21:

( i ) SEQUENCE CHARACTERISTICS:
      ( A ) LENGTH: 35 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "DNA"

( x i ) SEQUENCE DESCRIPTION: SEQ ID NO:21:

TTCATGAATA CTATTCGACT CACTATAGGA GATAT   35

( 2 ) INFORMATION FOR SEQ ID NO:22:

( i ) SEQUENCE CHARACTERISTICS:
      ( A ) LENGTH: 35 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "DNA"

( x i ) SEQUENCE DESCRIPTION: SEQ ID NO:22:

GTCCCTAAAT TAATACGACT CACTATAGGG AGATA   35

( 2 ) INFORMATION FOR SEQ ID NO:23:

( i ) SEQUENCE CHARACTERISTICS:
      ( A ) LENGTH: 35 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "DNA"

( x i ) SEQUENCE DESCRIPTION: SEQ ID NO:23:

GCCGGGAATT TAATACGACT CACTATAGGG AGACC   35

( 2 ) INFORMATION FOR SEQ ID NO:24:

( i ) SEQUENCE CHARACTERISTICS:
      ( A ) LENGTH: 35 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "DNA"

( x i ) SEQUENCE DESCRIPTION: SEQ ID NO:24:

ACTTCGAAAT TAATACGACT CACTATAGGG AGACC   35

( 2 ) INFORMATION FOR SEQ ID NO:25:

( i ) SEQUENCE CHARACTERISTICS:
    ( A ) LENGTH: 35 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:25:

GGCTCGAAAT TAATACGACT CACTATAGGG AGAAC    35

( 2 ) INFORMATION FOR SEQ ID NO:26:

( i ) SEQUENCE CHARACTERISTICS:
    ( A ) LENGTH: 35 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:26:

GCGTACCAAA TAATACGACT CACTATAGGG AGAGG    35

( 2 ) INFORMATION FOR SEQ ID NO:27:

( i ) SEQUENCE CHARACTERISTICS:
    ( A ) LENGTH: 35 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:27:

CACGATAAAT TAATACGACT CACTATAGGG AGAGG    35

( 2 ) INFORMATION FOR SEQ ID NO:28:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:28:

TATTAACCCT CACTAAAGGG AGA    23

( 2 ) INFORMATION FOR SEQ ID NO:29:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:29:

GTCTATTTAC CCTCACTAAA GGGAATAAGG    30

( 2 ) INFORMATION FOR SEQ ID NO:30:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "DNA"

( x i ) SEQUENCE DESCRIPTION: SEQ ID NO:30:

TAGCATTAAC CCTCACTAAC GGGAGACTAC 30

( 2 ) INFORMATION FOR SEQ ID NO:31:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:31:

TACAGTTAAC CCTCACTAAC GGGAGAGTTA 30

( 2 ) INFORMATION FOR SEQ ID NO:32:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:32:

AAGTAATAAC CCTCACTAAC AGGAGAATCC 30

( 2 ) INFORMATION FOR SEQ ID NO:33:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:33:

GGGCATTAAC CCTCACTAAC AGGAGACACA 30

( 2 ) INFORMATION FOR SEQ ID NO:34:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:34:

GCCTAATTAC CCTCACTAAA GGGAACAACC 30

( 2 ) INFORMATION FOR SEQ ID NO:35:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "DNA"

( x i ) SEQUENCE DESCRIPTION: SEQ ID NO:35:

TACAATTAAC CCTCACTAAA GGGAAGAGGG 30

( 2 ) INFORMATION FOR SEQ ID NO:36:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:36:

TCTAATTAAC CCTCACTAAA GGGAGAGACC 30

( 2 ) INFORMATION FOR SEQ ID NO:37:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:37:

ACCTAATTAC CCTCACTAAA GGGAGACCTC 30

( 2 ) INFORMATION FOR SEQ ID NO:38:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:38:

GTGAATTAAC CCTCACTAAA GGGAGACACT 30

( 2 ) INFORMATION FOR SEQ ID NO:39:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:39:

TTGCATTAAC CCTCACTAAA GGGAGAGAGG 30

( 2 ) INFORMATION FOR SEQ ID NO:40:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:40:

ATTTAGGTGA CACTATAGAA GGG     23

( 2 ) INFORMATION FOR SEQ ID NO:41:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:41:

ACACATACGA TTTAGGTGAC ACTATAGAAT ACAA     34

( 2 ) INFORMATION FOR SEQ ID NO:42:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:42:

TAATTGCCTA TTTAGGTGAC ACTATAGAAG GGAG     34

( 2 ) INFORMATION FOR SEQ ID NO:43:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:43:

GGACTTGGTA ATTAGGGGAC ACTATAGAAG GAGG     34

( 2 ) INFORMATION FOR SEQ ID NO:44:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:44:

GTGTCTCTTA TTTAGGGGAC ACTATAGAAG AGAG     34

( 2 ) INFORMATION FOR SEQ ID NO:45:

( i ) SEQUENCE CHARACTERISTICS:
 ( A ) LENGTH: 9 base pairs
 ( B ) TYPE: nucleic acid
 ( C ) STRANDEDNESS: single
 ( D ) TOPOLOGY: linear ( i i ) MOLECULE TYPE: other nucleic acid
 ( A ) DESCRIPTION: /desc = "DNA"

( x i ) SEQUENCE DESCRIPTION: SEQ ID NO:45:

GGTGACACT 9

( 2 ) INFORMATION FOR SEQ ID NO:46:

( i ) SEQUENCE CHARACTERISTICS:
 ( A ) LENGTH: 9 base pairs
 ( B ) TYPE: nucleic acid
 ( C ) STRANDEDNESS: single
 ( D ) TOPOLOGY: linear ( i i ) MOLECULE TYPE: other nucleic acid
 ( A ) DESCRIPTION: /desc = "DNA"

( x i ) SEQUENCE DESCRIPTION: SEQ ID NO:46:

CGACTCACT 9

( 2 ) INFORMATION FOR SEQ ID NO:47:

( i ) SEQUENCE CHARACTERISTICS:
 ( A ) LENGTH: 9 base pairs
 ( B ) TYPE: nucleic acid
 ( C ) STRANDEDNESS: single
 ( D ) TOPOLOGY: linear ( i i ) MOLECULE TYPE: other nucleic acid
 ( A ) DESCRIPTION: /desc = "DNA"

( x i ) SEQUENCE DESCRIPTION: SEQ ID NO:47:

ACCCTCACT 9

( 2 ) INFORMATION FOR SEQ ID NO:48:

( i ) SEQUENCE CHARACTERISTICS:
 ( A ) LENGTH: 9 base pairs
 ( B ) TYPE: nucleic acid
 ( C ) STRANDEDNESS: single
 ( D ) TOPOLOGY: linear ( i i ) MOLECULE TYPE: other nucleic acid
 ( A ) DESCRIPTION: /desc = "DNA"

( x i ) SEQUENCE DESCRIPTION: SEQ ID NO:48:

GGGCACACT 9

( 2 ) INFORMATION FOR SEQ ID NO:49:

( i ) SEQUENCE CHARACTERISTICS:
 ( A ) LENGTH: 9 base pairs
 ( B ) TYPE: nucleic acid
 ( C ) STRANDEDNESS: single
 ( D ) TOPOLOGY: linear ( i i ) MOLECULE TYPE: other nucleic acid
 ( A ) DESCRIPTION: /desc = "DNA"

( x i ) SEQUENCE DESCRIPTION: SEQ ID NO:49:

CAACTCACT 9

( 2 ) INFORMATION FOR SEQ ID NO:50:

( i ) SEQUENCE CHARACTERISTICS:
   ( A ) LENGTH: 9 base pairs
   ( B ) TYPE: nucleic acid
   ( C ) STRANDEDNESS: single
   ( D ) TOPOLOGY: linear ( i i ) MOLECULE TYPE: other nucleic acid
   ( A ) DESCRIPTION: /desc = "DNA"

( x i ) SEQUENCE DESCRIPTION: SEQ ID NO:50:

CGACTCAGT                                                                                          9

( 2 ) INFORMATION FOR SEQ ID NO:51:

( i ) SEQUENCE CHARACTERISTICS:
      ( A ) LENGTH: 9 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "DNA"

( x i ) SEQUENCE DESCRIPTION: SEQ ID NO:51:

GAACTCACT                                                                                          9

( 2 ) INFORMATION FOR SEQ ID NO:52:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "DNA"

( x i ) SEQUENCE DESCRIPTION: SEQ ID NO:52:

TAATACGACT CACTATAG                                                                                18

( 2 ) INFORMATION FOR SEQ ID NO:53:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "DNA"

( x i ) SEQUENCE DESCRIPTION: SEQ ID NO:53:

GGCAACGACC CCTCGTCA                                                                                18

( 2 ) INFORMATION FOR SEQ ID NO:54:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "DNA"

( x i ) SEQUENCE DESCRIPTION: SEQ ID NO:54:

TAATACGACT CACAATAT                                                                                18

( 2 ) INFORMATION FOR SEQ ID NO:55:

( i ) SEQUENCE CHARACTERISTICS:
  ( A ) LENGTH: 23 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "DNA"

( x i ) SEQUENCE DESCRIPTION: SEQ ID NO:55:

AATTAGGGCA CACTATAGGG AGA    23

( 2 ) INFORMATION FOR SEQ ID NO:56:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:56:

TAATACGACT CACTAATGCG AGA    23

( 2 ) INFORMATION FOR SEQ ID NO:57:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:57:

TATTAGGNCT CACTATAGGG AGG    23

( 2 ) INFORMATION FOR SEQ ID NO:58:

( i ) SEQUENCE CHARACTERISTICS:
    ( A ) LENGTH: 46 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:58:

ATTATGCTGA GTGATATCTA GCATGGTACC AACCGGCGTC ACAATA    46

( 2 ) INFORMATION FOR SEQ ID NO:59:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE: RNA ( x i ) SEQUENCE DESCRIPTION: SEQ ID NO:59:

GAUCGUACCA UGGUUGGCCG CAGUGUUAU    29

( 2 ) INFORMATION FOR SEQ ID NO:60:

( i ) SEQUENCE CHARACTERISTICS:
  ( A ) LENGTH: 43 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "DNA"

( x i ) SEQUENCE DESCRIPTION: SEQ ID NO:60:

TAGAAGTAAA CATATAATAC GACTCACTAT AGGCATTAGG AAT    43

( 2 ) INFORMATION FOR SEQ ID NO:61:

( i ) SEQUENCE CHARACTERISTICS:
    ( A ) LENGTH: 43 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:61:

ATCTTCATTT GTATCATTGT CTGAGTGTTA TACGTAATCC TTA    43

( 2 ) INFORMATION FOR SEQ ID NO:62:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( i i ) MOLECULE TYPE: RNA ( x i ) SEQUENCE DESCRIPTION: SEQ ID NO:62:

UGCAUUAGGA AU    12

( 2 ) INFORMATION FOR SEQ ID NO:63:

( i ) SEQUENCE CHARACTERISTICS:
    ( A ) LENGTH: 43 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:63:

CTCAGGTCAC TCTTTTAATA CGACTCACTA TAGCAATAAA GAT    43

( 2 ) INFORMATION FOR SEQ ID NO:64:

( i ) SEQUENCE CHARACTERISTICS:
    ( A ) LENGTH: 43 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:64:

GAGTCCAGTG AGAAACCGTT GCTGGGGAGC AGTGTTATTT CTA    43

( 2 ) INFORMATION FOR SEQ ID NO:65:

( i ) SEQUENCE CHARACTERISTICS:

(A) LENGTH: 11 base pairs
(B) TYPE: nucleic acid
(C) STRANDEDNESS: single
(D) TOPOLOGY: linear (ii) MOLECULE TYPE: RNA (xi) SEQUENCE DESCRIPTION: SEQ ID NO:65:

ACAAUAAAGA U                                                                                    11